US012702644B2

(12) United States Patent
Argañarás et al.

(10) Patent No.: US 12,702,644 B2
(45) Date of Patent: Aug. 11, 2026

(54) PHARMACEUTICAL COMPOSITION COMPRISING IBUPROFEN AND ARGININE

(71) Applicant: MACROBREATH CORPORATION, Dover, DE (US)

(72) Inventors: Luis Alberto Argañarás, Córdoba (AR); Nicolas Martinez Rios, Tigre Buenos Aires (AR)

(73) Assignee: INSPIRANOX THERAPEUTICS CORPORATION, Dover, DE (US)

( * ) Notice: Subject to any disclaimer, the term of this patent is extended or adjusted under 35 U.S.C. 154(b) by 253 days.

(21) Appl. No.: 18/713,885

(22) PCT Filed: Dec. 1, 2022

(86) PCT No.: PCT/IB2022/061638

§ 371 (c)(1),
(2) Date: May 28, 2024

(87) PCT Pub. No.: WO2023/100127

PCT Pub. Date: Jun. 8, 2023

(65) Prior Publication Data

US 2025/0032410 A1 Jan. 30, 2025

Related U.S. Application Data

(60) Provisional application No. 63/284,909, filed on Dec. 1, 2021.

(51) Int. Cl.

| | |
|---|---|
| ***A61K 9/08*** | (2006.01) |
| ***A61K 9/00*** | (2006.01) |
| ***A61K 9/19*** | (2006.01) |
| ***A61K 31/192*** | (2006.01) |
| ***A61K 31/198*** | (2006.01) |
| ***A61K 47/02*** | (2006.01) |
| ***A61P 11/00*** | (2006.01) |

(52) U.S. Cl.

CPC .............. *A61K 9/08* (2013.01); *A61K 9/0078* (2013.01); *A61K 31/192* (2013.01); *A61K 31/198* (2013.01); *A61K 47/02* (2013.01); *A61P 11/00* (2018.01); *A61K 9/19* (2013.01)

(58) Field of Classification Search

CPC ................................ A61K 9/08; A61K 31/192
USPC ......................................................... 424/400
See application file for complete search history.

(56) References Cited

U.S. PATENT DOCUMENTS

| | | | | |
|---|---|---|---|---|
| 10,973,787 | B2 | 4/2021 | Argañarás et al. | |
| 2012/0076859 | A1* | 3/2012 | Hofmann ............. | A61K 31/197 514/564 |
| 2015/0105468 | A1* | 4/2015 | Martinez-Alzamora .................... | A61P 27/02 514/570 |

FOREIGN PATENT DOCUMENTS

| | | | | |
|---|---|---|---|---|
| EP | 1439830 B1 | | 10/2005 | |
| EP | 3360547 A1 | | 8/2018 | |
| RU | 2012151921 A | * | 6/2014 | ................ A61P 3/04 |

OTHER PUBLICATIONS

Oscar Salva, et al., "Reversal of SARS-CoV2-Induced Hypoxia by Nebulized Sodium Ibuprofenate in a Compassionate Use Program", Infectious Diseases and Therapy, vol. 10, No. 4, pp. 2511-2524, 2021.
Ayobami Adebayo, et al., "L-Arginine and COVID-19: An Update", Nutrients, vol. 13, Issue No. 11, Article No. 3951, pp. 1-9, 2021.
Dimitrios Tsikas, et al., "GC-MS and GC-MS/MS measurement of ibuprofen in 10-µL aliquots of human plasma and mice serum using [a-methylo-2H3 ]ibuprofen after ethyl acetate extraction and pentafluorobenzyl bromide derivatization: Discovery of a collision energy-dependent H/D isotope effect and pharmacokinetic application to inhaled ibuprofen-arginine in mice" Journal of Chromatography B, vol. 1043, pp. 158-166, 2016.
International Search Report and Written Opinion for Corresponding International Application No. PCT/IB2022/061638, 9 pages, Feb. 16, 2023.

* cited by examiner

*Primary Examiner* — Walter E Webb
(74) *Attorney, Agent, or Firm* — LUCAS & MERCANTI, LLP

(57) ABSTRACT

A pharmaceutical composition to be applied to the pulmonary epithelium for the treatment of pulmonary diseases, comprising ibuprofen, arginine, solubilized in a hypertonic alkaline aqueous solution.

42 Claims, 4 Drawing Sheets

| ITEM | MEAS | PRED | PRED% |
|---|---|---|---|
| FVC(L) | 2.27 | 2.62 | 86.56% |
| FEV1(L) | 1.49 | 2.20 | 67.76% |
| FEV1/FVC(%) | 65.64 | 78.94 | 85.31% |
| PEF(L/s) | 3.86 | 5.88 | 65.65% |
| FEF2575(L/s) | 1.22 | 2.77 | 44.06% |
| FEF25(L/s) | 2.21 | 5.22 | 42.37% |
| FEF50(L/s) | 1.31 | 3.53 | 37.12% |
| FEF75(L/s) | 0.59 | 1.21 | 48.72% |
| EV(ml) | 26.00(1.15%FVC) | -- | -- |
| FET(s) | 9.02 | 6.00 | 150.33% |
| EOTV(ml) | 28.00 | -- | -- |
| PEFT(ms) | 57.00 | -- | -- |

| ITEM | MEAS | PRED | PRED% |
|---|---|---|---|
| FVC(L) | 2.22 | 2.62 | 84.69% |
| FEV1(L) | 1.53 | 2.20 | 69.55% |
| FEV1/FVC(%) | 68.92 | 76.94 | 89.57% |
| PEF(L/s) | 3.73 | 5.88 | 63.44% |
| FEF2575(L/s) | 1.34 | 2.77 | 48.38% |
| FEF25(L/s) | 2.64 | 5.02 | 48.60% |
| FEF50(L/s) | 1.43 | 3.53 | 40.52% |
| FEF75(L/s) | 0.62 | 1.21 | 51.20% |
| EV(ml) | 26.00(1.17%FVC) | ~ | ~ |
| FET(s) | 7.90 | 6.00 | 131.67% |
| EOTV(ml) | 26.00 | ~ | ~ |
| FEPT(ms) | 80.00 | ~ | ~ |

| LPS | - | + | + | + | + | + | + |
|---|---|---|---|---|---|---|---|
| Ibu 10 μM | - | - | + | - | - | - | - |
| Ibu 50 μM | - | - | - | + | - | - | - |
| Ibu 100 μM | - | - | - | - | + | - | - |
| Arg 50 μM | - | - | - | - | - | + | - |
| Apocynin | - | - | - | - | - | - | + |

| LPS | - | + | + | + | + | + | + | + | + | + |
|---|---|---|---|---|---|---|---|---|---|---|
| Ibu 10 μM | - | - | + | + | + | + | + | + | + | - |
| Arg 5 μM | - | - | - | + | - | - | - | - | - | - |
| Arg 10 μM | - | - | - | - | + | - | - | - | - | - |
| Arg 20 μM | - | - | - | - | - | + | - | - | - | - |
| Arg 50 μM | - | - | - | - | - | - | + | - | - | - |
| Arg 65 μM | - | - | - | - | - | - | - | + | - | - |
| Arg 85 μM | - | - | - | - | — | - | - | - | + | - |
| Apocynin | - | - | - | - | - | - | - | - | - | + |

PHARMACEUTICAL COMPOSITION COMPRISING IBUPROFEN AND ARGININE

FIELD OF INVENTION

The present invention relates to pharmaceutical compositions for the treatment of respiratory diseases and of epithelial tissue such as COVID-19 infections, acute respiratory distress syndrome (ARDS), chronic obstructive pulmonary disease (COPD), respiratory viral, bacterial and fungal infections, cystic fibrosis (CF), among others.

STATE OF THE ART

Non-steroidal anti-inflammatory drugs (NSAIDs) are a heterogeneous group of drugs that share their therapeutic action (analgesic, anti-inflammatory, and antipyretic effect), but differ in their relative toxicity and efficacy. The ibuprofen molecule with a molecular weight of 206.3 g/mol, as well as other derivatives of 2-arylpropionate, including ketoprofen, flurbiprofen, naproxen, etc., contains a chiral carbon in the alpha position of the propionate.

Ibuprofen is used as an antipyretic and for the symptomatic relief of headache (cluster), dental pain, muscle pain or myalgia, menstrual discomfort, mild neurological pain, and post-surgical pain. It is also used to treat inflammatory conditions such as those present in arthritis, rheumatoid arthritis, and gouty arthritis.

L-arginine is a semi-essential endogenous amino acid that plays an important role in cell division, wound healing, removal of ammonia from the body, immune function, hormone release, and is also the only biological precursor of nitric oxide (NO).

Nitric oxide (NO), which is produced from L-arginine by a family of isoenzymes called nitric oxide synthases (NOSs), plays an essential role in a variety of biological processes in the lung including host defense against pathogens, smooth muscle relaxation, bronchodilation, and inflammation [Ricciardolo, F. L. M. et al. (2004). Nitric Oxide in Health and Disease of the Respiratory System. *Physiological Reviews,* 84 (3), 731-765. https://doi.org/10.1152/physrev.00034.2003].

In the vascular endothelium, NO has shown antithrombotic and antimicrobial properties. In this regard, NO release from endothelium and platelets plays a crucial role in maintaining fluidity and preventing coagulation. NO-induced vasodilation helps to eliminate "microaggregates" and inhibits platelet adhesion and aggregation, preventing vascular occlusion [Izzo J. L. (2008). Hypertension primer: [the essentials of high blood pressure; basic science population science and clinical management] (4. ed.). Lippincott Williams & Wilkins]. On the other hand, virucidal and bactericidal effects have also been described in the literature. The antibacterial effect of NO has been demonstrated against infection-causing pathogens such as *Staphylococcus aureus, Staphylococcus epidermis, Pseudomonas aeruginosa, Escherichia coli, Acinetobacter baumanii, Listeria monocytogenes*, and *Enterococcus faecalis*. The antimicrobial mechanisms of NO include nitrosation of amines and thiols in the extracellular matrix, lipid peroxidation and tyrosine nitration in the cell wall, and DNA cleavage in the cell matrix [Pant, J. et al. (2017). Tunable Nitric Oxide Release from S-Nitroso-N-acetylpenicillamine via Catalytic Copper Nanoparticles for Biomedical Applications. *ACS Applied Materials and Interfaces,* 9 (18), 15254-15264. https://doi.org/10.1021/acsami.7b01408]. In addition, the ability of NO to suppress the replication of a respiratory coronavirus, which is unique to NO among other vasodilators, has been reported. [De Mel, A. (2020). Potential roles of nitric oxide in COVID-19: A perspective. *Integrative Molecular Medicine,* 7 (3). https://doi.org/10.15761/imm.1000403].

In the lungs, NO serves diverse purposes. For example, it functions as a selective pulmonary vasodilator to improve oxygenation and reduce pulmonary vascular resistance [Star, R. A. (1993). Southwestern internal medicine conference: Nitric oxide. *American Journal of the Medical Sciences,* 306(5), 348-358. https://doi.org/10.1097/00000441-199311000-00015.—Tripathi, P. (2007). Nitric oxide and immune response. *Indian Journal of Biochemistry & Biophysics,* 44 (5), 310-319.—Susswein, A. J., Katzoff, A., Miller, N., & Hurwitz, I. (2004). Nitric Oxide and Memory. *The Neuroscientist,* 10 (2), 153-162. https://doi.org/10.1177/1073858403261226.—Robbins, R. A., & Grisham, M. B. (1997). Nitric Oxide. *Int. J. Biochem. Cell Bid,* 29 (6), 857-860. https://doi.org/10.1016/S1357-2725 (96) 00167-7]. As a bronchial/airway dilator, NO promotes oxygen inhalation, increasing blood flow in the capillaries which exchange gas with the alveoli and accelerating the oxygen circulation in the body [Fang, W. et al. (2021). The role of NO in COVID-19 and potential therapeutic strategies. *Free Radical Biology and Medicine,* 163, 153-162. https://doi.org/10.1016/j.freeradbiomed.2020.12.008]. As a regulator of the immune system, it has been recognized that NO performs many functions where there are large numbers of cells in the system that produce and respond to NO [Tripathi, P., Tripathi, P., Kashyap, L., & Singh, V. (2007). The role of nitric oxide in inflammatory reactions. *FEMS Immunology and Medical Microbiology,* 51 (3), 443-452. https://doi.org/10.1111/j.1574-695X.2007.00329.x]. As a vascular anticoagulant, it inhibits blood coagulation and excessive platelet activation. And as an anti-inflammatory molecule, it prevents excessive inflammation through early non-specific immunity and regulates vascular inflammation and proliferation of immune cells [Fang, W. et al. (2021). The role of NO in COVID-19 and potential therapeutic strategies. *Free Radical Biology and Medicine,* 163, 153-162. https://doi.org/10.1016/j.freeradbiomed.2020.12.008].

In patients with cystic fibrosis (CF), higher concentrations of exhaled NO are closely related to improvement in lung function [Grasemann, H. et al. (1997). Decreased Concentration of Exhaled Nitric Oxide (NO) in Patients With Cystic Fibrosis. *Pediatric Pulmonology,* 24 (3), 173-177. https://doi.org/10.1002/(sici)1099-0496(199709)24:3<173::aid-ppul2>3.0.co; 2-o-Ho, L. P. et al. (1998). Exhaled nitric oxide is not elevated in the inflammatory airways diseases of cystic fibrosis and bronchiectasis. *European Respiratory Journal,* 12 (6), 1290-1294. https://doi.org/10.1183/09031936.98.12061290—Keen, C. et al. (2010). Low levels of exhaled nitric oxide are associated with impaired lung function in cystic fibrosis. *Pediatric Pulmonology,* 45(3), 241-248. https://doi.org/10.1002/ppul.21137]. Indeed, Ratjen and cols. [Grasemann, H. et al. (2006). Inhaled L-arginine improves exhaled nitric oxide and pulmonary function in patients with cystic fibrosis. *American Journal of Respiratory and Critical Care Medicine,* 174(2), 208-212. https://doi.org/10.1164/rccm.200509-1439OC] found that the administration of L-arginine inhalation therapy resulted in a transient improvement in the pulmonary function of CF patients. In later studies [Grasemann, H. et al. (2013). A randomized controlled trial of inhaled I-Arginine in patients with cystic fibrosis. *Journal of Cystic Fibrosis,* 12(5), 468-474. https://doi.org/10.1016/j.jcf.2012.12.008], they found that L-arginine inhalation was well tolerated and resulted in a significant increase in exhaled NO. FEV1 increased by an average of 56 ml compared to −8 ml after saline solution, but this difference did not reach statistical significance. Moreover, there was no change in inflammatory markers in sputum. They concluded that the repeated inhalation of L-arginine alone in patients with CF was safe and well tolerated. Inhaled L-arginine increased NO production but no evidence of changes in airway inflammation was found. It is interesting to note that they opted to use a twice-daily inhalation of 5 mL of a 100 mg/mL solution, resulting in a cumulative daily dose of 1 g L-arginine. They showed that, after 14 days of inhalation treatment with a high concentration of L-arginine, there was a measurable increase in the concentrations of the NOS inhibitor ADMA and the L-arginine/ADMA ratio (NOS substrate over inhibitor), which is decreased in CF patients and correlates with low airway NO. However, the study found that the potential effect of increased L-arginine concentrations is counteracted by an increase in both L-ornithine, which competes with L-arginine for transport into the cell, and ADMA, which acts as a competitive NOS inhibitor.

Another article studied the supplementation of gaseous NO to treat antibiotic-resistant bacterial and fungal lung infections in patients with cystic fibrosis [Deppisch, C. et al. (2016). Gaseous nitric oxide to treat antibiotic resistant bacterial and fungal lung infections in patients with cystic fibrosis: a phase I clinical study. *Infection,* 44 (4), 513-520. https://doi.org/10.1007/s15010-016-0879-x]. In this article, the authors reported large reductions in bacterial numbers that led to reduced pulmonary inflammation and increases in the lung function parameter FEV1 from baseline to a degree seldom observed after antibiotic therapy courses in CF patients. Nonetheless, the fact that treatment with gaseous NO for long periods of time would unequivocally lead to the formation of toxic $NO_2$ levels, MetHb, and hypoxemia, represents a major disadvantage of this treatment alternative.

On the other hand, it has also been shown that NO can have detrimental effects on the organism of people suffering from pulmonary diseases. For example, asthmatic patients have higher concentrations of exhaled NO than healthy people and it is known that reactive nitrogen species are involved in the pathogenesis of asthma and the development of "nitrosative stress" [Kleniewska, P., & Pawliczak, R. (2017). The participation of oxidative stress in the pathogenesis of bronchial asthma. *Biomedicine and Pharmacotherapy,* 94, 100-108. https://doi.org/10.1016/j.biopha.2017.07.066]. In patients with pneumonia by COVID-19, high production of reactive species oxygen (ROS) and reactive nitrogen species (RNS, e g., nitric oxide (NO)) can lead to septic shock [Chavarria, A. P. et al. (2021). Antioxidants and pentoxifylline as coadjuvant measures to standard therapy to improve prognosis of patients with pneumonia by COVID-19. *Computational and Structural Biotechnology Journal,* 19, 1379-1390. https://doi.org/10.1016/j.csbj.2021.02.009]. Moreover, cells that are damaged due to NO production express nitrotyrosine which, in turn, can have a pathogenic effect due to its ability to react with many different molecules [Adebayo, A., Varzideh, F., Wilson, S., Gambardella, J., Eacobacci, M., Jankauskas, S. S., Donkor, K., Kansakar, U., Trimarco, V., Mone, P., Lombardi, A., & Santulli, G. (2021). L-arginine and covid-19: An update. *Nutrients,* 13(11). https://doi.org/10.3390/nu13113951].

In summary, NO has many beneficial effects that can be useful to treat lung diseases; however, an excess of NO can also lead to cytotoxic effects causing oxidative damage and cell death. Whether or not NO has a toxic or protective effect depends on many factors.

Oxidative stress is caused by an excessive systemic manifestation of reactive oxygen species (ROS) compared to a reduced capacity of a biological system to rapidly neutralize the reactive intermediates or repair the resulting damage. Increased ROS concentrations are capable of reducing the amount of bioactive NO by chemical inactivation to form toxic peroxynitrite. Peroxynitrite, in turn, can "uncouple" endothelial NO synthase and become a dysfunctional superoxide-generating enzyme that further contributes to vascular oxidative stress [Förstermann, U. (2010). Nitric oxide and oxidative stress in vascular disease. *Pflugers Archiv European Journal of Physiology,* 459(6), 923-939. https://doi.org/10.1007/s00424-010-0808-2]. In this vein, a correlation between the presence of systemic or local oxidative stress and various pulmonary diseases, including all those treated in the examples herein, has been described in the literature [Ornatowski, W. et al. (2020). Complex interplay between autophagy and oxidative stress in the development of pulmonary disease. Redox Biology, 36. https://doi.org/10.1016/j.redox.2020.101679—Zinellu, E. et al. (2021). Oxidative stress biomarkers in chronic obstructive pulmonary disease exacerbations: A systematic review. Antioxidants, 10(5), 710. https://doi.org/10.3390/antiox10050710—Farouk, A. et al. (2016). Role of oxidative stress and outcome of various surgical approaches among patients with bullous lung disease candidate for surgical interference. Journal of Thoracic Disease, 8(10), 2936-2941. https://doi.org/10.21037/jtd.2016.10.41—Bai, Y. et al. (2018). A Chinese herbal formula ameliorates pulmonary fibrosis by inhibiting oxidative stress via Upregulating Nrf2. Frontiers in Pharmacology, 9(JUN). https://doi.org/10.3389/fphar.2018.00628—Horvath, I. et al. (1998). Increased levels of exhaled carbon monoxide in bronchiectasis: A new marker of oxidative stress. Thorax, 53(10), 867-870. https://doi.org/10.1136/thx.53.10.867—Jesenak, M. et al. (2017). Oxidative stress and bronchial asthma in children-causes or consequences? Frontiers in Pediatrics, 5. https://doi.org/10.3389/fped.2017.00162—Nikolova, G. D. et al. (2018). Oxidative stress and related diseases. Part 1: Bronchial asthma. Bulgarian Chemical Communications, 50, 30-35—Fernandes, I. G. et al. (2020). SARS-CoV-2 and Other Respiratory Viruses: What Does Oxidative Stress Have to Do with It? Oxidative Medicine and Cellular Longevity, 2020. https://doi.org/10.1155/2020/8844280—Chavarria, A. P. et al. (2021). Antioxidants and pentoxifylline as coadjuvant measures to standard therapy to improve prognosis of patients with pneumonia by COVID-19. Computational and Structural Biotechnology Journal, 19, 1379-1390. https://doi.org/10.1016/j.csbj.2021.02.009], and therefore disease treatments targeting ROS inhibition and restoration of the oxidant/antioxidant imbalance have also been proposed.

In view of the present state of the art, it becomes apparent that there is a need for therapeutic treatments that, using low doses of active pharmaceutical ingredients, control oxidative stress in respiratory diseases. The present invention provides a solution to this problem, achieving its therapeutic effects by decreasing oxidative stress. The present invention surprisingly manages to reduce oxidative stress through the synergistic combination of ibuprofen with arginine in a hypertonic alkaline solution for nebulization. Achieving therapeutic effects never seen before in patients with various lung diseases.

Regarding ibuprofen and arginine combinations, several Ibuprofen-arginine formulations containing ibuprofen arginate salt (molar ratio 1:1) can be found in the market since that combination is characterized by rapid absorption and higher peak plasma concentrations of ibuprofen, as well as by lower $t_{max}$ values compared to the free acid form and other preparations [Cattaneo, D., & Clementi, E. (2010). Clinical Pharmacokinetics of Ibuprofen Arginine. *Current Clinical Pharmacology,* 5 (4), 239-245. https://doi.org/10.2174/157488410793352012]. On the other hand, a previous work [Tsikas, D. et al. (2017). GC-MS and GC-MS/MS measurement of ibuprofen in 10-μL aliquots of human plasma and mice serum using [α-methylo-2H3]ibuprofen after ethyl acetate extraction and pentafluorobenzyl bromide derivatization: Discovery of a collision energy-dependent H/D isotope effect and pharmacokinetic application to inhaled ibuprofen-arginine in mice. *Journal of Chromatography B: Analytical Technologies in the Biomedical and Life Sciences,* 1043, 158-166. https://doi.org/10.1016/j.jchromb.2016.06.014] discloses a method for the determination of ibuprofen in human plasma samples that was used to measure the concentration of ibuprofen in serum samples of mice upon inhalation of an ibuprofen arginate preparation in saline. However, said article does not anticipate or suggest the existence of a range of concentrations for the combination of ibuprofen and arginine that improves lung function in any pathology. In addition, it is worth noting that all these preparations are based on the ibuprofen arginate salt and therefore, the arginine/ibuprofen molar ratio is 1.

In contrast, the present invention provides a pharmaceutical composition comprising an arginine/Ibuprofen molar ratio, preferably lower than 6.5, and also preferably greater than 1, that has a synergistic effect on the inhibition of reactive oxygen species. Said pharmaceutical formulation can be administered by nebulization to treat different lung diseases such as; asthma, chronic obstructive pulmonary disease (COPD), cystic fibrosis (CF), pulmonary hypertension, bronchopulmonary dysplasia, acute respiratory distress syndrome (ARDS), respiratory syndrome coronavirus 2 (SARS-CoV-2), bilateral pneumonia, viral, bacterial and fungal lung infections and bronchiectasis, among others, improving oxygen saturation, respiratory rate, cardiac frequency, and blood pressure.

The pharmaceutical composition of the present invention shows important physiological benefits for treating lung diseases. This composition comprises very simple molecules like an anti-inflammatory (ibuprofen) and a basic amino acid (arginine) that, when combined at specific concentrations, ionic strength, and pH values, exhibits a synergic effect in the synthesis and release of nitric oxide (NO), which also improve the vasodilation. Moreover, the presence of Arginine formulated together with Ibuprofen to be nebulized, not only affects NO levels but also has a marked synergistic effect on the reduction of oxidative stress, as shown in the examples herein. As a consequence, it induces an improvement in the $O_2$ saturation, causing an increase in the pulmonary function (FEV1) in patients. This protective strategy is associated with reduced acute lung injury (ALI). This synergistic effect is achieved at much lower arginine concentrations than those used in other treatments, it is longer lasting, and no inhibiting effects have been observed in sustained treatments over time.

In addition, this composition contains an anti-inflammatory molecule such as Ibuprofen which has also shown bactericidal properties against Gram+ and Gram-bacteria, especially by inhibiting bacteria such as *P. aeruginosa, S. aureus, B. cepacia* and also having a virucidal effect on those lipid-enveloped viruses [Argañarás, L. A. et al. (2021). Bactericidal and virucidal pharmaceutical composition. DC: U.S. Patent and Trademark Office. U.S. Pat. No. 10,973,787 B2—García, N. H. et al. (2020). Ibuprofen, a traditional drug that may impact the course of COVID-19 new effective formulation in nebulizable solution. *Medical Hypotheses,* 144. https://doi.org/10.1016/j.mehy.2020.110079]. Furthermore, the pharmaceutical composition of the present invention comprises a dissolved salt in a composition such that the synergistic bactericidal and antiviral effect disclosed in the patent U.S. Pat. No. 10,973,787 B2 is achieved, boosting the overall bactericidal and virucidal effect of said pharmaceutical composition and making it more suitable for the treatment of lung diseases caused by pathogens.

BRIEF DESCRIPTION OF THE INVENTION

A pharmaceutical composition to be applied on the pulmonary epithelium for the treatment of respiratory or lung diseases, main object of the present invention, comprises ibuprofen, arginine, solubilized in a hypertonic aqueous solution at a pH between 7.5 and 9.5 wherein the arginine/ibuprofen molar ratio is preferably lower than 6.5 and preferably greater than 1. Wherein more preferably the arginine/ibuprofen molar ratio is from 1.5 and 5, wherein preferably is from 2 to 5, more preferably 2. Wherein the ibuprofen is in a concentration from 10 mM to 50 mM, and wherein said ibuprofen is racemic, or is the S enantiomer, or is the R enantiomer. Wherein said ibuprofen comprises, as a counterion, the monovalent cation selected from the group comprising sodium, potassium, lithium, arginate, lysinate, histidinate and combinations thereof. And said arginine comprises a concentration from 10 mM to 250 mM.

In a preferred embodiment of the present invention, said formulation further comprises a pH in aqueous solution of 8.0 to 9.0, preferably of 8.5.

The composition of the present invention is administered by nebulization or inhalation and comprises a state selected from the group comprising liquid, powder and lyophilized state.

In a preferred embodiment, said composition is hypertonic because it comprises a salt in a concentration from 0.3 to 2.0 M, preferably from 0.4 to 1.1 M, more preferably from 0.5 to 1.0 M. Said salt is suitable for human consumption and is selected from the group comprising sodium chloride, potassium chloride, sodium carbonate and combinations thereof. Preferably, said salt is NaCl.

The pharmaceutical composition is useful for the treatment of lung disease such as; asthma, chronic obstructive pulmonary disease (COPD), cystic fibrosis (CF), pulmonary hypertension, and bronchopulmonary dysplasia, acute respiratory distress syndrome (ARDS), respiratory syndrome coronavirus 2 (SARS-CoV-2), viral, bacterial and fungal lung infections, bilateral pneumonia and bronchiectasis.

In another embodiment, the pharmaceutical composition to be applied on the pulmonary epithelium for the improvement of lung function, comprises ibuprofen, arginine, solubilized in a hypertonic aqueous solution at a pH between 7.5 and 9.5 wherein the arginine/ibuprofen molar ratio is greater than 1 and lower than 6.5.

In another embodiment, the pharmaceutical composition to be applied on the pulmonary epithelium for the improvement of lung function, comprises ibuprofen, arginine, solubilized in a hypertonic aqueous solution at a pH between 7.5 and 9.5 wherein the arginine/ibuprofen molar ratio is greater than 1 and lower than 6.5 and wherein the ibuprofen concentration is between 10 mM and 50 mM and the arginine concentration is between 10 mM and 250 mM.

Another object of the present invention is a manufacturing process of a pharmaceutical composition with bactericidal, virucidal and anti-inflammatory properties to be applied on epithelial tissue such as pulmonary tissue, which comprises the following steps:

a) mixing said ibuprofen in its acid state with aqueous solution of $Na_2CO_3$ at more than 40° C. and stirring to maintain its suspension;
b) adding said arginine on the step a);
c) adding NaOH or $Na_2CO_3$ to reach a pH value from 7.5 to 9.5 and stirring to allow a complete solubilization of said ibuprofen and arginine to obtain a concentration between 1 and 100 mg/mL for ibuprofen and between 5 and 100 mg/mL for basic amino acid;
d) adding said salt suitable for human consumption to the preparation of said step c), in a concentration from 0.3 to 1.0 M and;
e) filtering the preparation in said step d), through a 0.22 micron pore filter.

Optionally, said process comprises the following steps:

f) lyophilizing the filtered solution in said step e),
g) at the time to be applied, resuspending the lyophilized composition of said step f) in water or in a 2.5% of glucose solution.

Another object of the present invention is a method for treating lung disease comprising administering an effective amount the pharmaceutical composition to the pulmonary epithelium of the subject; wherein the pharmaceutical composition is administered to the subject as a nebulized solution. In one embodiment, between 1 mL and 25 mL of the pharmaceutical composition is administered to the subject; preferably, between 1 mL and 10 mL; more preferably, between 1 mL and 5 mL. More preferably 3 mL of the pharmaceutical composition is administered to the subject.

Said lung disease is selected from the group comprising; asthma, chronic obstructive pulmonary disease (COPD), cystic fibrosis (CF), pulmonary hypertension, and bronchopulmonary dysplasia, acute respiratory distress syndrome (ARDS), respiratory syndrome coronavirus 2 (SARS-CoV-2), viral, bacterial and fungal lung infections, bilateral pneumonia and bronchiectasis.

Wherein the subject is hypoxic, or has a pulse-oximetry blood-oxygen saturation level of less than 92%, or has a respiratory rate of 21-25 breaths/minute, or has a respiratory rate of 25-30 breaths/minute, or has a respiratory rate of 30-40 breaths/minute, or has a respiratory rate over 41 breaths/minute, or has a pulse rate of 91-110 beats/minute, or has a pulse rate of 111-130 beats/minute, or has a pulse rate of over 131 beats/minute, or has a NEWS2 Score of 0-4, or has a NEWS2 Score of 5-6, or has a NEWS2 Score of 7 or greater, is intubated, is pre-intubation, or is non-hypoxic.

DETAILED DESCRIPTION OF THE INVENTION

Figure 1:
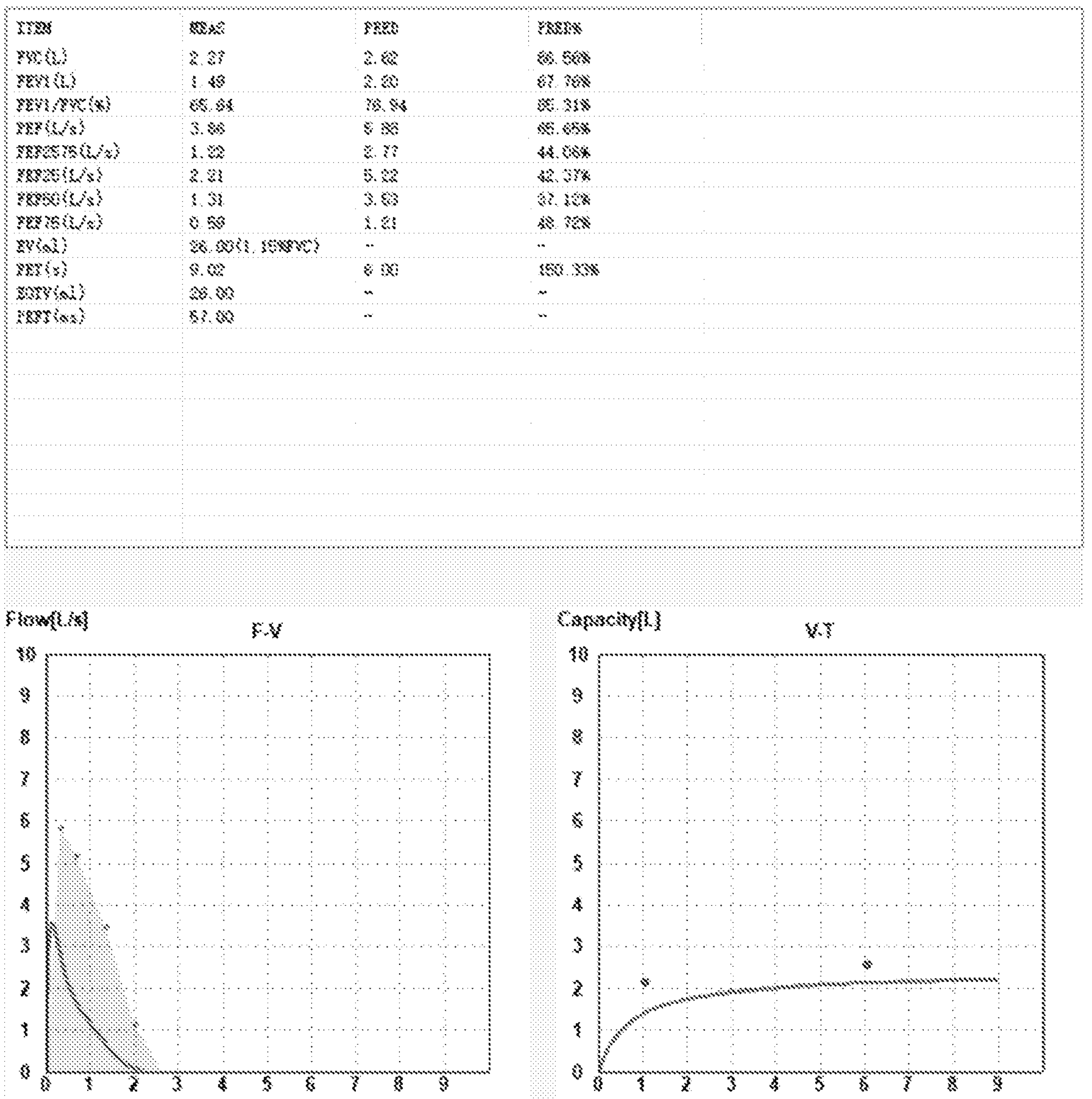
FIG. 1. Pre-nebulization spirometry test results of subject 9.

A pharmaceutical composition to be applied on the pulmonary epithelium, main object of the present invention, comprises a non-steroidal anti-inflammatory drug (NSAID), a basic amino acid, solubilized in an aqueous solution at alkaline pH between 7.5 and 9.5.

"NSAID" refers to a non-steroidal anti-inflammatory drug which is selected from the group comprising ibuprofen, naproxen, flurbiprofen, ketoprofen, diclofenac, diflunisal, etodolac, fenoprofen, indomethacin, meclofenamate, mefenamic acid, meloxicam, oxaprozin, piroxicam, sulindac, celecoxib, acetylated salicylate, and combinations thereof. Wherein said NSAID, is in a concentration from 5 mM to 500 mM, preferably in a concentration from 5 mM to 180 mM, more preferably in a concentration from 5 mM to 50 mM. Said NSAID is in its deprotonated form, in which the proton is replaced with another cation. Said NSAID comprises as a counterion the monovalent cation selected from the group comprising sodium, potassium, lithium, arginate, lysinate, histidinate, and combinations thereof. In one embodiment, the preferred formulation comprises ibuprofen.

Given that ibuprofen has one chiral center, it has two possible enantiomers R and S. The invention contemplates the use of the R enantiomer, the use of the S enantiomer and mixtures thereof, including racemic mixtures (1:1 mixtures of the R and S enantiomers). The designation of the R enantiomer or the S enantiomer indicates an optical purity of at least 90%, 95%, 98%, or 99% by weight. "Optical purity" refers to the percent of the designated enantiomer relative to the combined weight of both enantiomers.

In the present invention, said ibuprofen to be solubilized in an aqueous solution can be added in its acid form or as a salt comprising as a counterion the monovalent cation selected from the group comprising sodium, potassium, lithium, arginate, lysinate, histidinate and combination thereof.

"Basic amino acids" refers to the amino acids that have basic side chains at neutral pH, such as; arginine, lysine, and histidine. Their side chains contain nitrogen and resemble ammonia, which is a base. In one embodiment, said basic amino acid, is in a concentration from 10 mM to 500 mM, preferably in a concentration from 25 mM to 300 mM, more preferably in a concentration from 50 mM to 250 mM, and even more preferably in a concentration from 80 mM to 150 mM. Where said basic amino acid is preferably arginine.

"Aqueous solution" refers to the solution that uses a polar liquid as a solvent, preferably water, and has the NSAID and the basic amino acid solubilized in it. In another embodiment, said aqueous solution further comprises a salt suitable for human consumption, preferably $Na_2CO_3$, KCl, or NaCl, more preferably NaCl. Wherein said aqueous solution is preferably hypertonic comprising a concentration of said salt suitable for human consumption from 0.3 M to 2 M, preferably from 0.4 M to 1.1 M, even more preferably from 0.5 M to 1.0 M. Alternatively, the molar ratio of said ibuprofen to salt (ibuprofen:amino acid) is from 1:0.6 to 1:400.

Furthermore, said pharmaceutical composition comprises a pH in aqueous solution between pH 7.5 and pH 9.5, preferably between pH 8 and pH 9, more preferably the pH of said pharmaceutical composition is 8.5.

The pharmaceutical composition of the invention is administered by inhalation or nebulization. Administering a formulation by "inhalation" refers to administering the formulation directly to the lungs through the mouth or/and nasal cavity, commonly by inhaling the formulation.

Administration of the pharmaceutical composition of the present invention can be accomplished by nebulization, in which a nebulizer changes liquid medicine into fine droplets (in aerosol or mist form) that are inhaled through a mouthpiece or mask. Nebulization can be accomplished by any suitable means, including by 1) jet, which uses compressed gas to make an aerosol (tiny particles of medication in the air or 2) ultrasound, which makes an aerosol through high-frequency vibrations. In one embodiment, the nebulization is carried out with a piston nebulizer. In one embodiment, the nebulized droplets are of a sufficient size to reach the alveoli.

Alternatively, the pharmaceutical composition may be delivered with an inhaler. In one example, the pharmaceutical formulation is administered through a metered dose inhaler (MDI), which "pushes out" a pre-measured spray of the pharmaceutical composition, with, for example, a hydrofluoroalkane aerosol spray. In another example, a soft mist inhaler (SMI) provides a pre-measured amount of the pharmaceutical formulation in a slow-moving mist.

Furthermore, the present invention may be prepared either in a liquid state or as a powder or lyophilized by drying or lyophilization from the final aqueous solution of said pharmaceutical composition. Both the drying process and the lyophilization of pharmaceutical composition are well known in the prior art, therefore providing further details on the subject is not considered necessary.

The present invention is a pharmaceutical composition that is useful for the treatment of lung diseases and viral or no-viral lung infections such as; asthma, chronic obstructive pulmonary disease (COPD), cystic fibrosis (CF), pulmonary hypertension, bronchopulmonary dysplasia, acute respiratory distress syndrome (ARDS), respiratory syndrome coronavirus 2 (SARS-CoV-2), bilateral pneumonia, and bronchiectasis.

Cystic fibrosis is a serious disease that mainly affects children. Is an inherited condition that causes sticky mucus to build up in the lungs and digestive system. This causes lung infections and problems with digesting food. Asthma is a disease of the respiratory system characterized by chronic inflammation of the airway that affects both children and adults. Chronic Obstructive Pulmonary Disease (COPD) is the name for a group of lung conditions that cause breathing difficulties. Is a common condition that mainly affects middle-aged or older adults who smoke. The breathing problems tend to get gradually worse over time. Pulmonary hypertension is high blood pressure in the blood vessels that supply the lungs (pulmonary arteries). It is a serious condition that can damage the right side of the heart. The walls of the pulmonary arteries become thick and stiff, and cannot expand as well to allow blood through.

Bronchopulmonary dysplasia (BPD) is a form of chronic lung disease that affects newborns, most often those who are born prematurely and need oxygen therapy. In BPD the lungs and the airways (bronchi) are damaged, causing tissue destruction (dysplasia) in the tiny air sacs of the lung (alveoli); acute respiratory distress syndrome (ARDS); occurs when fluid builds up in the tiny, elastic air sacs (alveoli) in your lungs. The fluid keeps the lungs from filling with enough air, which means less oxygen reaches the bloodstream. This deprives the organs of the oxygen they need to function.

Respiratory Syndrome Coronavirus 2 (SARS-CoV-2) is a recent virus disease where patients show pneumonia. In this case, fever was the most common symptom, followed by coughing. Most patients present lower values of $O_2$ saturation and less capability to breathe. Bilateral lung involvement with ground-glass opacity was the most common finding from computed tomography images of the chest.

The formulation of the present invention achieves the therapeutic effects described in the examples by acting on oxidative stress. Oxidative stress is caused by an excessive systemic manifestation of reactive oxygen species (ROS) compared to a reduced capacity of a biological system to rapidly neutralize the reactive intermediates or repair the resulting damage. In this vein, a relation between the presence of systemic or local oxidative stress and diverse lung diseases, including all the ones treated in the examples, have been described in the literature and, therefore, disease treatments targeting ROS inhibition and restoration of the oxidants/antioxidants imbalance have also been proposed.

For example, Ornatowski et al. [Ornatowski, W. et al. (2020). Complex interplay between autophagy and oxidative stress in the development of pulmonary disease. *Redox Biology,* 36. https://doi.org/10.1016/j.redox.2020.101679] discussed the interplay of ROS and autophagy in lung diseases including Chronic Obstructive Pulmonary Disease, Acute Lung Injury, Cystic Fibrosis, Idiopathic Pulmonary Fibrosis, Pulmonary Arterial Hypertension, and Asthma, and concluded that ROS-autophagy interaction plays a critical and complex role in the pathogenesis of these lung diseases. In particular, Zinellu et al. [Zinellu, E. et al. (2021). Oxidative stress biomarkers in chronic obstructive pulmonary disease exacerbations: A systematic review. *Antioxidants,* 10(5), 710. https://doi.org/10.3390/antiox10050710] reviewed articles related to oxidative stress biomarkers in exacerbated COPD patients compared to the stable phase of the disease, identifying reliable oxidative stress biomarkers that could be useful in monitoring disease progression in COPD patients and especially in those more susceptible to exacerbations. Farouk et al. [Farouk, A. et al. (2016). Role of oxidative stress and outcome of various surgical approaches among patients with bullous lung disease candidate for surgical interference. *Journal of Thoracic Disease,* 8(10), 2936-2941. https://doi.org/10.21037/jtd.2016.10.41] found significantly higher plasma levels of oxidative stress markers and lower antioxidant vitamins levels among the patients suffering from bullous lung disease when compared with the control group and proved that oxidative stress plays an important role in the pathogenesis of the disease.

Oxidative stress also plays important roles in the inflammation, collagen deposition, and fibrosis of pulmonary fibrosis lungs; and free radical activity, lipid products and oxidized proteins have been identified in exhaled air, bronchus alveolar lavage fluid, serum and lung of patients with pulmonary fibrosis [Bai, Y. et al. (2018). A Chinese herbal formula ameliorates pulmonary fibrosis by inhibiting oxidative stress via Upregulating Nrf2. *Frontiers in Pharmacology,* 9(JUN). https://doi.org/10.3389/fphar.2018.00628]. Likewise, it is known that the pathophysiology of bronchiectasis involves oxidative stress and oxidative stress biomarkers have been found in the breath of patients with bronchiectasis [Horvath, I. et al. (1998). Increased levels of exhaled carbon monoxide in bronchiectasis: A new marker of oxidative stress. *Thorax,* 53 (10), 867-870. https://doi.org/10.1136/thx.53.10.867].

Regarding bronchial asthma, it is generally accepted that oxidative stress represents an important part of its pathogenesis [Jesenak, M. et al. (2017). Oxidative stress and bronchial asthma in children-causes or consequences? *Frontiers in Pediatrics,* 5. https://doi.org/10.3389/fped.2017.00162]. Also, it has been confirmed that the development and maintenance of inflammatory processes in the respiratory tract are associated with the oxidative and nitrosative stress present in asthmatic patients [Nikolova, G. D. et al. (2018). Oxidative stress and related diseases. Part 1: Bronchial asthma. *Bulgarian Chemical Communications,* 50, 30-35].

In addition, respiratory viruses, comprising human respiratory syncytial virus (RSV), influenza (IV), human rhinovirus (HRV), human metapneumovirus (HMPV), parainfluenza, and adenoviruses and coronaviruses (CoVs), induce ROS-generating enzymes, such as nicotinamide adenine dinucleotide phosphate oxidases (NADPH oxidase, Nox) and xanthine oxidase (XO), while creating unbalanced antioxidant levels [Fernandes, I. G. et al. (2020). SARS-CoV-2 and Other Respiratory Viruses: What Does Oxidative Stress Have to Do with It? *Oxidative Medicine and Cellular Longevity,* 2020. https://doi.org/10.1155/2020/8844280].

Finally, patients with moderate and severe pneumonia by COVID-19 may develop sepsis. Sepsis has been the leading cause of mortality in intensive care units worldwide during the last pandemic. Septic shock is a consequence of sepsis, where there is a high production of ROS, and RNS (e g., nitric oxide (NO)) that can cause multiple organ failure (pulmonary, cardiac, neurological, and hepatic) [Chavarría, A. P. et al. (2021). Antioxidants and pentoxifylline as coadjuvant measures to standard therapy to improve prognosis of patients with pneumonia by COVID-19. *Computational and Structural Biotechnology Journal,* 19, 1379-1390. https://doi.org/10.1016/j.csbj.2021.02.009].

The present invention has advantages that had never been reported before since using very low doses of NSAID and basic amino acid, combined at specific concentrations and specific pH and salt concentration values, exhibits a synergic effect in the synthesis and release of nitric oxide (NO) and in the reduction of oxidative stress, which also improve the vasodilation and as consequence induce the improvement in the $O_2$ saturation and finally an increase of the pulmonary function FEV-1 in patients.

Technically, using very low concentrations of NSAIDs and the basic amino acid arginine, result in a synergic effect on $O_2$ saturation and FEV-1 and produce a decrease in blood pressure with a reduction of the common adverse effects of these anti-inflammatory drugs and on the other hand, the lower doses of arginine in this formulation prevent the increase of asymmetric dimethylarginine (ADMA), an inhibitor of endothelial NOS that appear when high doses of arginine were used.

Moreover, due to the nature of its composition, the present invention achieves the synergistic bactericidal and antiviral effects described in U.S. Pat. No. 10,973,787 B2, boosting the overall bactericidal and virucidal effect of said pharmaceutical composition and making it more suitable for the treatment of lung diseases caused by pathogens.

Another object of the present invention is a process of manufacturing a pharmaceutical composition to be applied to epithelial tissue such as pulmonary tissue, comprising the following steps:

a) mixing said NSAID with water and stirring to maintain its suspension;
b) adding said basic amino acid on the step a);
c) adding NaOH or $Na_2CO_3$ to reach a pH value from 7.5 to 9.5 and stirring to allow a complete solubilization of said ibuprofen and the basic amino acid to obtain a concentration between 1 and 100 mg/mL for NSAID and between 1 and 250 mg/mL for basic amino acid;
d) adding said salt suitable for human consumption to the preparation of said step c), in a concentration from 0.3 to 1.0 M and;
e) filtering the preparation in said step d), through a 0.22 micron pore filter.

In a preferred embodiment of the present invention, said process further comprises the following steps:

f) lyophilizing the filtered solution in said step e);
g) at the time to be applied, resuspending the lyophilized composition of said step f) in water or in a 2.5% of glucose solution.

In a more preferred embodiment, the process of manufacturing a pharmaceutical composition to be applied on epithelial tissue such as pulmonary tissue, comprises the following steps:

a) dissolving NaOH or $Na_2CO_3$ in 70% of the final volume of purified water, heated at 45° C.;
b) adding the NSAID (sifted to a fine powder) to the solution of step a) and stirring until dissolution;
c) adding the basic amino acid to the solution of step b);
d) adding salt suitable for human consumption to the solution step c) and stir until dissolution;
e) adding NaOH or $Na_2CO_3$ solution to the solution of step d) to reach a pH value from 7.5 to 9.5;
f) cooling the solution obtained in step e) to room temperature and adding purified water to complete the final volume of the solution, obtaining a concentration between 1 and 100 mg/mL of said NSAID, a concentration between 1 and 250 mg/ml of said basic amino acid, and a concentration from 0.3 to 1.0 M of salt suitable for human consumption;
g) filtering the preparation obtained in step f), through a 0.22 micron pore filter.

In an even more preferred embodiment of the present invention, said process further comprises the following steps:

h) lyophilizing the filtered solution in said step e);
i) at the time to be applied, resuspending the lyophilized composition of said step h) in water or in a 2.5% of glucose solution.

Another object of the present invention is directed to the use of the pharmaceutical composition for the treatment of the lung diseases previously mentioned in a subject.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

"Treat," "treating," or "treatment," when used in connection with a subject with a lung disease, includes improving the effects or symptoms of the disease or shortening the duration of said disease. In instances where the subject has become hypoxic, "treat," "treating," or "treatment," refers to returning blood oxygenation to normal or near normal more rapidly than in the absence of treatment. In instances where the subject has progressed to severe disease, "treat," "treating," or "treatment," refers to lessening the likelihood of requiring intubation, decreasing the time requiring intubation, decreasing recovery time, and/or reducing the mortality rate.

"Effective amount" means an amount when administered to the subject with a lung disease which results in beneficial or desired results, including improvement of the effects or symptoms of said lung diseases, including normalizing blood oxygenation levels, shortening recovery time, decreasing the likelihood of requiring intubation in severe disease and/or decreasing mortality.

The precise amount of the pharmaceutical solution administered to provide an "effective amount" to the subject will depend on the type, and severity of the lung disease, and on the characteristics of the subject, such as general health, age, sex, body weight, and tolerance to drugs. The skilled artisan will be able to determine appropriate dosages depending on these and other factors. Suitable dosages are known for approved therapeutic agents and can be adjusted by the skilled artisan according to the condition of the subject, the type of lung disease being treated and the amount of pharmaceutical composition being used by following, for example, dosages reported in the literature and recommended in the Physician's Desk Reference (57th ed., 2003). For example, an "effective amount" can be between 1 mL to 50 mL of the pharmaceutical composition used in the disclosed methods. Alternatively, an "effective amount" is between 1 mL to 25 mL of the pharmaceutical composition used in the disclosed methods. In another alternative, "effective amount" is between 1 mL and 10 mL of the pharmaceutical composition used in the disclosed methods. In another alternative, "effective amount" is between 3 mL and 7 mL of the pharmaceutical composition used in the disclosed methods. In yet another alternative, an "effective amount" is 3 mL of the pharmaceutical composition used in the disclosed methods. An effective amount is administered between 1 and 5 times daily, alternatively from 1 to 3 times daily. The time of administration varies between 5 minutes and 1 hour and alternatively between 5 minutes and 30 minutes. In yet another alternative, the time of administration varies between 10 minutes and 20 minutes.

A small but significant percentage of subjects with a respiratory viral infection progress to severe and even life-threatening disease such as pneumonia or acute respiratory distress syndrome (ARDS) (referred to herein as "severe disease"). Pneumonia is an infection that inflames the air sacs (alveoli) in one or both lungs. The air sacs may fill with fluid or pus (purulent material), causing cough with phlegm or sputum, fever, chills, and difficulty breathing. ARDS is also characterized by fluid build-up in the air sacs in the lungs, but it is also accompanied by hyperinflammation, which may induce a condition sometimes referred to as "cytokine storm" or systemic inflammation which can lead to respiratory failure and death. Symptoms of ARDS include severe shortness of breath, labored and unusually rapid breathing, low blood pressure and/or confusion and extreme tiredness.

Low blood oxygenation levels also accompany pneumonia and ARDS and are responsible, at least in part, for the severe symptoms associated with these conditions. Oxygen saturation levels offer an integrated assessment of pulmonary and cardiac function, and its non-invasive measurement with transdermal pulse oximetry has become a routine component of the assessment of disease severity. "Low blood oxygenation levels in a subject refers to a pulse-oximetry oxygen saturation level of less than 95%, the lower limit of normal for healthy subjects (patients with hypercapnic respiratory disease live with lower chronic oxygen saturation levels). Oxygen saturation of <92% is considered an urgent matter, requiring immediate intervention, particularly when this reflects an acute change from baseline normal values as is often observed in patients with viral pneumonitis. A subject with a low blood oxygenation level is also referred to herein as being "hypoxic". Subjects with respiratory viral infection diseases who have progressed to pneumonia or ARDS, when treated according to the disclosed methods, have shown improved blood oxygenation, including restoration of blood oxygenation levels to normal and with relief of the severe symptoms associated with ARDS.

A second common measure of cardiopulmonary status is the respiratory rate, which in healthy adults is typically less than or equal to 20 breaths/minute. Subjects with respiratory viral infections that have progressed to pneumonia or ARDS frequently present with respiratory rates far above the normal range (up to 21-25 breathes/minute, 25-30 breathes/minute or, in more severe cases, 30 to 40 breaths/minute), and such subjects, when treated according to the disclosed methods, have shown improvement in respiratory rate to the normal range. This is one component of the alleviation of severe symptoms associated with ARDS described above.

A third measure of cardiopulmonary status is the heart rate, which in healthy adults at rest is typically less than 90 beats per minute, but may be markedly elevated in subjects with respiratory viral infections that have progressed to pneumonia or ARDS. Subjects with respiratory viral infections that have progressed to pneumonia or ARDS frequently present with heart rates far above the normal range (from 91-110 beats/minute, in more severe cases from 111-130 beats/minute, to over 131 beats/minute in the most severe cases). Subjects with viral pneumonia or ARDS, when treated according to the disclosed methods, have shown improvement in heart rate to the normal range.

The National Early Warning Score (NEWS2) is an accepted assessment tool for identifying subjects who have or are likely to develop an acute illness. See, for example, Royal College of Physicians, National Early Warning Score (NEWS) 2: Standardizing the Assessment of Acute-Illness Severity in the NHS. Updated Report of the Working Party, London: RCP, 2017. Specifically, a NEWS2 Score of 0-4 indicates a low level of clinical risk for the subject; a NEWS2 Score of 5-6 indicates a moderate level of clinical risk for the subject; and a NEWS2 Score of 7 or more indicates a high level of clinical risk for the subject. The disclosed methods can be used to treat a subject with a NEWS2 Score of 0-4, 5-6 or 7 or more to reduce the likelihood of increasing the scope or to reduce the score to bring the subject to an improved condition with a lower score.

In particularly severe cases, subjects with ARDS require breathing assistance and are put on a mechanical ventilator, i.e., the subject is "intubated". The disclosed methods can increase blood oxygenation and are useful in reducing the likelihood that a hypoxic subject with severe disease who is not yet intubated will subsequently require intubation. The disclosed methods are also useful in increasing blood oxygenation in intubated patients, thereby increasing the likelihood of recovery and decreasing the amount of time the subject spends on a ventilator.

In some instances, subjects with lung diseases who are experiencing only mild symptoms may nonetheless be hypoxic, i.e., have low blood oxygen levels. The low blood oxygenation levels are an indication that the subject with only mild symptoms is at risk for progressing to severe disease, such as pneumonia or ARDS. The disclosed methods of treatment are effective in reducing the likelihood that hypoxic subjects experiencing only mild symptoms will progress to severe disease such as pneumonia or ARDS. As noted above, the disclosed methods of treatment have also been shown to be effective in treating subjects who are hypoxic and who have already developed more severe disease such as pneumonia or ARDS.

The disclosed methods can also be used to treat non-hypoxic subjects with lung diseases who are experiencing only mild symptoms to reduce the likelihood of these subjects becoming hypoxic and/or progressing to severe disease.

Considering the information previously mentioned and the results shown in the examples (see below), It has been demonstrated that the composition of the present invention shows important improvement for the treatments of various diseases that affect the lungs, such as: asthma, chronic obstructive pulmonary disease (COPD), cystic fibrosis (CF), pulmonary hypertension, bronchopulmonary dysplasia, acute respiratory distress syndrome (ARDS), respiratory syndrome coronavirus 2 (SARS-CoV-2), bilateral pneumonia, and bronchiectasis, among others. In all these pathologies the nebulization with this composition containing a mix of Ibuprofen-arginine-salt at a pH of 8.5, produces a substantial anti-inflammatory effect and an improvement of oxygen saturation, respiratory rate, heart rate, and blood pressure.

EXAMPLES

Example 1: Preparation of Alkaline Hypertonic Ibuprofen (AHI) Solution for Tests Performed in the Following Examples Add to a suitable container, water for injection corresponding to 70% of the final volume of the batch. Then proceed to incorporate and dissolve the amount of sodium carbonate necessary for the preparation of the batch. This process is carried out by mechanical agitation and avoiding contamination and loss of the solution.

Once the sodium carbonate is dissolved, add the ibuprofen with strong agitation. Agitate until complete dissolution.

Add the sodium citrate and, once it has dissolved, add the sodium chloride, maintaining moderate agitation until the solution is homogeneous. Measure the pH of the solution. Adjust the pH of the solution to 8.6±0.1 at 25° C., adding a 10% sodium carbonate solution as needed.

After adjusting the pH, add purified water to reach the final volume of the solution.

TABLE 1

Composition of alkaline hypertonic ibuprofen (AHI) solution.

| | Every 5 mL (mg) | Every 5 mL (mmol) | Concentration (mg/mL) | Concentration (mM) |
|---|---|---|---|---|
| Ibuprofen | 50.00 | 0.242 | 10.00 | 48.48 |
| Sodium Chloride | 146.10 | 2.500 | 29.22 | 500.00 |
| Sodium Carbonate | 30.00 | 0.283 | 6.00 | 56.61 |
| Sodium Citrate | 10.00 | 0.039 | 2.00 | 7.75 |
| Sodium Hydroxide | 9.75 | 0.244 | 1.95 | 48.75 |
| Water purified q.s. | 5.00 | 0.277 | — | — |

Example 2: Preparation of the Favorite Formulation of the Present Invention (Ibu-Arg Solution)

The preferred method of preparation of the formulation used for the embodiment of the present invention, which proves to be the best known to the inventors, is described, but is not the only possible one.

a) dissolving $Na_2CO_3$ in 70% of the final volume of purified water, heated at 45° C.;

b) adding the ibuprofen (sifted to a fine powder) to the solution of step a) and stirring until dissolution;

c) adding the arginine hydrochloride to the solution of step b);

d) adding NaCl to the solution of step c) and stirring until dissolution.

e) adding $Na_2CO_3$ solution to the solution of step d) to reach a pH value of 8.5;

f) cooling the solution obtained in step e) to room temperature and adding purified water to complete the final volume of the solution;

g) filtering the preparation obtained in step f), through a 0.22 micron pore filter.

TABLE 2

Composition of the Favorite Formulation of the Present Invention.

| | Every 5 mL (mg) | Every 5 mL (mmol) | Concentration (mg/mL) | Concentration (mM) |
|---|---|---|---|---|
| Ibuprofen | 50.0 | 0.242 | 10.0 | 48.48 |
| Arginine Hydrochloride | 102.2 | 0.485 | 20.4 | 97.03 |
| Sodium Chloride | 146.1 | 2.500 | 29.2 | 500.00 |
| Sodium Carbonate | 30.0 | 0.283 | 6.0 | 56.61 |
| Water purified q.s. | 5.0 | 0.277 | | |

Example 3: Effect of Nebulization with AHI Solution Containing Increasing Concentrations of Arginine on the $O_2$ Saturation, Heart Rate and Respiratory Rate in a COVID-19 Positive Subject In this and the following example, the "RF" values refer to respiratory rate and are given in breaths/minute. The "CFq" values refer to heart rate in beats/minute. The "$PO_2$" values refer to $O_2$ saturation, measured by pulse oximetry and expressed in percentage. The "BP" values refer to systolic/diastolic blood pressure and are expressed in mmHg. The term "HBP" means high blood pressure.

Subject 1.

Gender: female.

Age: 62 years old.

Admission date: Aug. 20, 2021; discharge date: Sep. 3, 2021.

Diagnosis: mild bilateral pneumonia by SARS-CoV-2.

Pathological personal history: type 2 diabetes and obesity.

Clinical Evolution of Subject 1:

Admission in Hospital: Aug. 20, 2021 (had been with COVID-19 for 8 days). The $PO_2$ was 92-93% at room air, without oxygen supplementation. The RF was 22 and the CFq was 89. The subject receives oxygen supplementation (low flow $O_2$ 2 L/h) and support treatment with dexamethasone and heparin. The subject received nebulization treatment with AHI solution every 8 h from Aug. 20, 2021 to Aug. 28, 2021.

At 11 AM on Aug. 28, 2021, the subject received a nebulization treatment with 3 mL of AHI solution containing 6 mM of L-Arginine Hydrochloride. No substantial changes were observed, after 6 hs the $PO_2$ remained at 93%.

At 5 PM on Aug. 28, 2021, the subject received a nebulization treatment with 3 mL of AHI solution containing 12 mM of L-Arginine Hydrochloride. After nebulization RF was 22, the CFq was 86, and $PO_2$ was still at 93%.

At 11 PM on Aug. 28, 2021, the subject received a nebulization treatment with 3 mL of AHI solution containing 25 mM of L-Arginine Hydrochloride. $PO_2$ remained at 93-94%.

At 6 AM of Aug. 29, 2021, the subject received a nebulization treatment with 3 mL of AHI solution containing 50 mM of L-Arginine Hydrochloride. After nebulization, the RF was 22, the CFq was 86, and $PO_2$ rose to 96% and remained at 96% for at least 6 hours.

At 12 AM on Aug. 29, 2021, the subject received a nebulization treatment with 3 mL of AHI solution containing 100 mM of L-Arginine Hydrochloride. After nebulization, the RF was 18-19, the CFq was 75-76, and $PO_2$ increased again, reaching values of 98-99% which were maintained for 8 to 10 h.

The subject continued this treatment and was discharged on Sep. 3, 2021. No adventitious or "added" sounds were observed. The subject reported feeling much better. No adverse effects were observed during the treatment.

Example 4: Effect of Nebulization with the Favorite Formulation (Ibu-Arg Solution) of the Present Invention on $O_2$ Saturation, Heart Rate and Respiratory Rate in Three Subjects COVID-19 Positive Subject 2.

- Gender: female.
- Age: 52 years old.
- Admission date: Aug. 31, 2021; discharge date: Sep. 6, 2021.
- Diagnosis: mild bilateral pneumonia by SARS-COV-2.
- Pathological personal history: obesity (+); type 2 diabetes (+).

Clinical Evolution of Subject 2:

Admission in Hospital: Aug. 31, 2021 (had been with COVID-19 for 8 days). The $PO_2$ was 91-93% at room air. The RF was 20 and the CFq was 69. The subject receives oxygen supplementation (low flow $O_2$ 2 L/h) and support treatment with dexamethasone and heparin. Adventitious sounds were observed: bibasilar crackles, right predominance. The subject received nebulizations with AHI solution every 6 h from Aug. 24, 2021 to Aug. 31, 2021.

On Aug. 31, 2021 the subject started receiving a nebulization treatment with 3 mL of Ibu-Arg solution every 8 h. At the end of nebulization, $PO_2$ was 97%, without $O_2$ supplementation. Eight hours after nebulization, $PO_2$ was 95%, without $O_2$ supplementation.

The subject continued this treatment and was discharged on Sep. 6, 2021 with $PO_2$=97%, RF=18, and CF=88. No presence of adventitious or "added" sounds were observed at this point.

Subject 3.

- Gender: male.
- Age: 61 years old.
- Admission date: Aug. 21, 2021; discharge date: Sep. 26, 2021.
- Diagnosis: bilateral pneumonia with moderate/severe pattern (TAC) by SARS-CoV-2.
- Pathological personal history: HBP (+).

Clinical Evolution of Subject 3:

Admission in Hospital: Aug. 21, 2021. The $PO_2$ was 93%, RF was 21, and CFq was 70. The subject receives oxygen supplementation (intermittent $O_2$, according to the patient's needs) and support treatment with dexamethasone and heparin. Observations: decrease of vesicular murmur, marked dyspnea. The subject received nebulization treatment with AHI solution every 8 h from Aug. 14, 2021 to Aug. 21, 2021.

On Aug. 21, 2021 the subject started receiving a nebulization treatment with 3 mL of Ibu-Arg solution every 8 h and the $PO_2$ reached 98%. 8 h after nebulization, $PO_2$ was 95%.

The subject continued this treatment and was discharged on Sep. 26, 2021 with $PO_{2=97}$%, RF=20, and CF=68. No presence of adventitious or "added" sounds were observed at this point.

Subject 4.

- Gender: Male.
- Age: 52 years old.
- Admission date: Aug. 31, 2021; discharge date: Sep. 6, 2021.
- Diagnosis: severe bilateral pneumonia by SARS-COV-2.
- Pathological personal history: type 1 diabetes.

Clinical Evolution of Subject 4:

Admission in Hospital: Aug. 31, 2021 (had been with COVID-19 for 8 days). The $PO_2$ was 88-90% at room air. The RF was 22 and the CFq was 88. The subject receives oxygen supplementation (low flow oxygen 2 L/h) and support treatment with dexamethasone and heparin. The subject had a fever, headache, and global hypoventilation; also adventitious sounds were observed: bibasilar crackles. The subject started receiving nebulizations with AHI solution every 6 h on Aug. 26, 2021.

On Aug. 31, 2021 the subject started receiving a nebulization treatment with 3 mL of Ibu-Arg solution every 6 h and the $PO_2$ reached 94%. Six hours after nebulization, $PO_2$ was 91%.

The subject continued this treatment and was discharged on Sep. 6, 2021 with $PO_2$=97%, RF=17, and CF=74. No presence of adventitious or "added" sounds were observed at this point.

Example 5: Effect of Nebulization with the Favorite Formulation (Ibu-Arg Solution) of the Present Invention on $O_2$ Saturation, Heart Rate, and Respiratory Rate in a Subject with Scar Pulmonary Fibrosis Subject 5.

- Gender: female.
- COVID-19 test: negative (−).
- Date: Sep. 10, 2021.
- Age: 77 years old; weight: 54 kg; height: 1.46 m.
- Diagnostic: scar pulmonary fibrosis, traction bronchiectasis.
- Evolution: at the age of 48 she inhaled acids (peridol, hydrochloric and sulfuric acid) in a laboratory incident.
- Pathological personal history: surgeries (appendectomy, amygdalectomy, cholecystectomy); type 2 diabetes (+); HBP (+).
- Toxic background: tobacco (+) (20 cigarettes a day for 16 years, quit 30 years ago); alcohol (+); drugs (+) (in the laboratory incident).
- Treatment: Atrovent (Ipratropium Bromide) SOS; physiotherapy. Oxygen supplementation: 4 liters during the night, less amount during daytime.
- Basal state: $PO_2$=91-90-86%, RF=24, CFq=115, BP=110/80 with $O_2$ backpack. $PO_2$ decreased to 82% without $O_2$ backpack.

Clinical Evolution of Subject 5:

The subject started receiving nebulizations with AHI solutions seven months ago. It improved $O_2$ saturation from 84% to 90% and lowered oxygen requirements. The subject could not speak, not even on the phone.

On Sep. 10, 2021, the subject started receiving a nebulization treatment with 3 mL of Ibu-Arg solution every 12 h. The $PO_2$ increased to 96% and CFq decreased to 110.

One hour after nebulization, RF was 24, CFq was 102, and $PO_2$ was 92% (without $O_2$ backpack). The subject did not cough. The subject can speak, subjective improvement and objective clinical improvement were observed.

Example 6: Effect of Nebulization with the Favorite Formulation (Ibu-Arg Solution) of the Present Invention on $O_2$ Saturation, Heart Rate, and Respiratory Rate in a Subject with Chronic Obstructive Pulmonary Disease (COPD)

Subject 6.

Gender: male.

COVID-19 (rapid) test: negative (−).

Admission date: Sep. 10, 2021; discharge date: Sep. 25, 2021.

Age: 79 years old; weight: 60 kg; height: 1.69 m.

Diagnosis: COPD; emphysema; bibasal pulmonary fibrosis.

Evolution: from 2007 the subject was a passive smoker (kitchen ovens fumes).

Pathological personal history: before starting treatment with AHI, the subject suffered from repeated bacterial pneumonias (two per year) that required hospitalization. Cholecystectomy surgery; type 2 diabetes; HBP.

Toxic background: tobacco (−); alcohol (+); drugs (−).

Treatment: indacaterol capsules every 12 hours; hexaler (Desloratadine) every 12 hours.

Clinical Evolution of Subject 6:

Two years ago, the subject started receiving nebulizations with 5 mL of AHI solutions every 8 hs (basal state: $PO_2$=94%, RF=20, CFq=72, BP=140/80). Since then, the subject never required hospital admission again. The subject had only one episode of pneumonia that was overcome with antibiotic therapy. The subject manifests having continuous white secretions.

On Sep. 10, 2021, the subject started receiving a nebulization treatment with 5 mL of Ibu-Arg solution every 8 h. During nebulization, the $PO_2$ reaches values of 95-97% and CFq was 71. The nebulization was briefly interrupted to expectorate.

One hour after nebulization the $PO_2$ was 96% and CFq was 71. Clinical improvement is observed.

The subject continued this treatment and was discharged on Sep. 25, 2021.

Example 7: Effect of Nebulization with the Favorite Formulation (Ibu-Arg Solution) of the Present Invention on $O_2$ Saturation, Heart Rate, and Respiratory Rate in a Subject with Bronchiectasis Subject 7.

Gender: female.

COVID-19 (rapid) test: Negative (−).

Date of medical visit: Sep. 10, 2021.

Age: 72 years old; weight: 58 kg; height: 1.57 m.

Diagnosis: central cylindrical bronchiectasis (some isolated by traction). History of a lung infection without medication.

Evolution of disease: since 2013.

Pathological personal history: surgeries (−); diabetes (−); HBP (+). Two eutocic deliveries.

Toxic background: tobacco (−); alcohol (−); drugs (−); stress (+).

Treatment: seretide 250 (fluticasone/salmeterol) every 12 h.

Clinical Evolution of Subject 7:

Eight months ago, the subject started receiving nebulizations with 3 mL of AHI solutions every 12 hs (basal state: $PO_2$=94%, RF=18, CFq=77, BP=125/70). This treatment allowed to reduce the dose of seretide.

On Sep. 10, 2021, the subject received a nebulization treatment with 3 mL of Ibu-Arg solution. During nebulization, the $PO_2$ reached 99% and CFq was 75. The subject had no coughing spells.

One hour after nebulization the $PO_2$ was 98% and CFq was 68. Great clinical improvement was observed.

Example 8: Effect of Nebulization with the Favorite Formulation (Ibu-Arg Solution) of the Present Invention on $O_2$ Saturation, Heart Rate, Respiratory Rate, and Blood Pressure in a Subject with Bullous Emphysema Subject 8.

Gender: male.

COVID-19 test: negative (−).

Date: Sep. 11, 2021.

Age: 72 years old; weight: 65 kg; height: 1.76 m.

Diagnostic: severe bullous emphysema.

Evolution: the subject was diagnosed with COPD 12 years ago but he has had episodes of dyspnea since 1977.

Pathological personal history: surgeries (cholecystectomy, adenoma of prostate, hernia); diabetes (+) and HBP (+). Brain Vascular Accident in 2010.

Background: COVID-19 (+), which was treated with nebulization with hypertonic alkaline ibuprofen (AHI) solution.

Toxic background: tobacco (+) (more than 60 cigarettes per day, he left 10 years ago), alcohol (+), drugs (−).

Treatment: indacaterol, frevia (budesonide/formoterol), SOS oxygen therapy, carvedilol, valsartan 160 mg.

Clinical Evolution of Subject 8:

One year ago, the subject started receiving nebulizations with 3 mL of AHI solutions every 8 hs (basal state: $PO_2$=90-92%, RF=24, CFq=76, BP=150/90). The subject noticed that the treatment made him dizzy, but improved oxygen saturation.

On Sep. 11, 2021, the subject received a nebulization treatment with 3 mL of Ibu-Arg solution. During nebulization the $PO_2$ increased to 96-97%, RF was 23, CFq was 72, and BP was 150/90. The treatment was well tolerated.

One hour after nebulization the $PO_2$ was 98%, RF was 21, CFq was 70, and BP was 130/80. No adverse effects were observed, and the subject was visibly excited.

Example 9: Effect of Nebulization with the Favorite Formulation (Ibu-Arg Solution) of the Present Invention on $O_2$ Saturation, Heart Rate, Respiratory Rate, and Blood Pressure in a Subject with Bronchial Asthma Subject 9.

Gender: female.

COVID-19 test: negative.

Date: Sep. 11, 2021 start nebulization with Ibu-Arg solution.

Age: 64 years; weight: 80 kg; height: 1.62 m.

Diagnostic: severe/moderate bronchial asthma with bronchial hyperresponsiveness (HRB)

Disease evolution: since childhood suffers from bronchial asthma. 35 years ago, during her last pregnancy, she began to suffer from respiratory insufficiency.

Pathological personal history: cesarean surgery for respiratory insufficiency; diabetes (+); HBP (+); obesity (+); stress (+++). Three pregnancies, two eutocic deliveries.

Background: COVID-19 (+), asymptomatic.

Toxic Background: tobacco (−), alcohol (−), drugs (−).

Treatment: neumoterol (micronized budesonide/micronized formoterol fumarate dihydrate) 1 per day.

Clinical Evolution of Subject 9:

Nine months ago, the subject started receiving nebulizations with AHI solutions (basal state: $PO_2$=94%, RF=21, CFq=74, BP=120/80). It reduced wheezing, could talk, reduced dyspnea on exertion, and coughing. Improves sleep quality, (she could not sleep on her back). The treatment allowed to decrease the dose of neumoterol. The subject still presented bronchospasms, wheezing, and cough.

On Sep. 11, 2021 the subject received a nebulization treatment with 3 mL of Ibu-Arg solution. During nebulization the $PO_2$ reached 99%, RF was 12, and CFq was 71. The treatment improved expiration and reduced itching.

One hour after nebulization the $PO_2$ was still at 99%, RF was 13, CFq was 71, and BP was 100/60. Subjective improvement and objective clinical improvement.

Walking test: $PO_2$ at rest was 96%-2 min: bronchospasm with basal wheezing $PO_{2=94}$%. After rest and recovery, $PO_2$ was 96%.

Post nebulization the subject climbed the stairs for the first time in many years, presenting an $O_2$ saturation of 97%.

Figure 2:
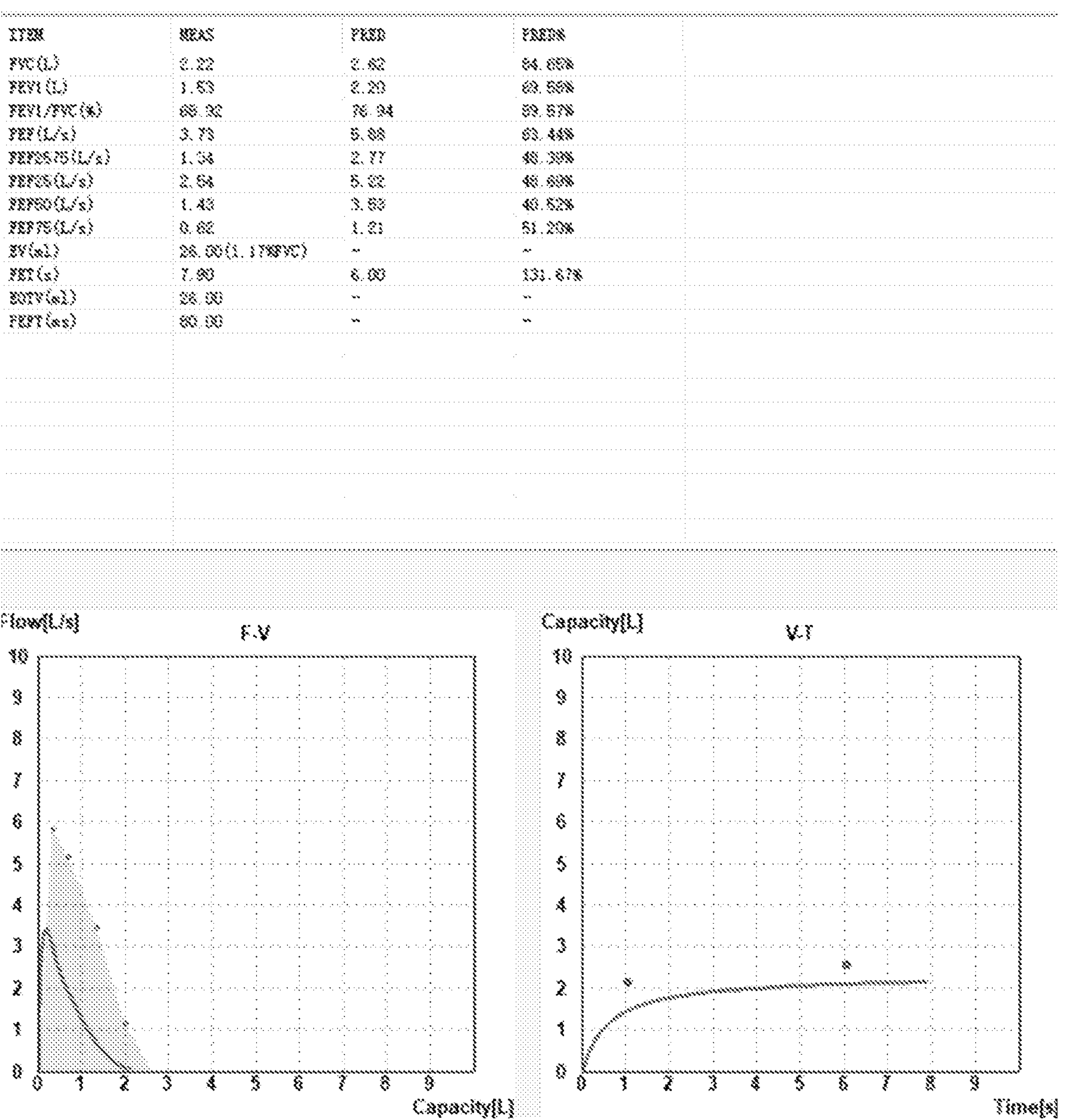
FIG. 2. Spirometry test results of subject 9, 60 minutes after nebulization with Ibu-Arg solution.

In addition, subject 9 was subjected to spirometry tests prior to nebulization and 60 minutes after nebulization with Ibu-Arg solution. The results of these tests are exhibited in FIGS. 1 and 2, respectively.

Example 10: Effect of Nebulization with the Favorite Formulation (Ibu-Arg Solution) of the Present Invention on $O_2$ Saturation, Heart Rate, Respiratory Rate, and Blood Pressure in a Subject with Post-COVID-19 Pulmonary Fibrosis Subject 10

Gender: female.

COVID-19 test: negative.

Age: 53 years old; weight: 83 kg (increased 20 Kg after COVID-19); height: 1.57 m.

Date of the assay: Sep. 11, 2021.

Diagnostic: post-COVID pulmonary fibrosis.

Evolution: COVID-19 Feb. 10, 2021-asymptomatic, the subject was nebulized every 8 hours with AHI solution.

The next week begins with post-COVID dyspnea and nebulizations. The subject is a sportswoman (biking, trekking, Crossfit).

Pathological personal history: cholecystectomy and hysterectomy surgeries. Post-COVID insulin-dependent diabetes. Previously suffered from type 2 diabetes (+). HBP (+).

Treatment: sertraline, topiramate (to treat dysthymia).

Toxic background: tobacco (−); alcohol (−); drugs (−).

Clinical Evolution of Subject 10:

Three months ago the subject started receiving nebulizations with 5 mL of AHI solutions every 8 h (basal state: $PO_{2=92}$-93%, RF=24, CFq=85, BP=120/90). The subject suffered from dyspnea.

On Sep. 11, 2021 the subject received a nebulization treatment with 3 mL of Ibu-Arg solution. During nebulization the $PO_2$ was 98-99%, RF was 18, and CFq was 80. The subject was less agitated.

Four hours after nebulization the $PO_2$ was still at 98-99%, RF was 17, CFq was 82, and BP was 110/70. The subject is not agitated and mentions that can breathe through the nose. Notable clinical improvement. The subject could climb up and down stairs.

Example 11: Effect of Nebulization with Arginine Solution at pH 7.0 and 8.5 and with the Favorite Formulation of the Present Invention on the $O_2$ Saturation, Heart Rate, Respiratory Rate, and Blood Pressure in a Subject with Bronchial Asthma Subject 11.

Gender: female.

Admission date: Sep. 28, 2021.

Age: 71 years old; weight: 78 kg; height: 1.62.

COVID-19 test: negative (−).

Diagnosis: Bronchial asthma 53 years ago.

Evolution: asthma that required hospitalization with oxygen therapy on several occasions; allergic to ambient dust HRB (+).

Pathological personal history: gallbladder surgery; diabetes (−); HBP (+); COVID-19 (+) hospitalization and treatment with AHI solution; post-COVID fatigue. Four pregnancies, three eutocic deliveries, one spontaneous abortion.

Toxic background: tobacco (+); alcohol (+); drugs (−).

Treatment: Seretide Diskus 500 (fluticasone/salmeterol).

Habitual $PO_2$ was 95%.

Clinical Evolution of Subject 11:

Basal state: $PO_2$=95%, RF=17, CFq=71, and BP=165/100. The subject suffered from Dyspnea.

The subject received a nebulization treatment with 3 ml of 100 mM arginine solution at pH 7. $PO_2$ remained at 95%, RF=19, CFq=63, and BP=160/100. No changes were observed after 2 h.

Later, the subject received a nebulization treatment with 3 ml of 100 mM arginine solution at pH 8.5. Once again $PO_2$ remained at 95% and no changes were observed after 2 h.

Finally, the subject received nebulization treatment with 3 ml of Ibu-Arg solution at pH 8.5. Immediately after nebulization: $PO_2$=100%, RF=18, CFq=67. Six hours after nebulization: $PO_2$=100%, RF=18, CFq=68. and BP=150/100. Eight hours after nebulization: $PO_2$ was still at 100%.

Example 12: Effect of Nebulization with Arginine Solution at pH 7.0 and 8.5 and with the Formulation of the Present Invention at pHs 8 and 8.5 on the $O_2$ Saturation, Heart Rate, Respiratory Rate, and Blood Pressure in a Subject with COPD Subject 12.

Gender: female.

Admission date: Sep. 28, 2021.

Age: 81 years old; weight: 75 kg; height: 1.64.

COVID-19 test: negative (−).

Diagnosis: COPD, dyspnea on exertion.

Pathological personal history: carpal tunnel surgery; diabetes (−); HBP (+); COVID (−). Two pregnancies, two eutocic labors.

Toxic background: tobacco (+) (20 cigarettes a day during 30 years); alcohol (−); drugs (−).

Treatment: neumoterol (micronized budesonide/micronized formoterol fumarate dihydrate).

Clinical Evolution of Subject 12:

Basal state: $PO_2$=93%, RF=20, CFq=78, and BP=135/74. The subject suffered from dyspnea on exertion. Some isolated rhonchi were also detected.

The subject received a nebulization treatment with 3 ml of 100 mM arginine solution at pH 7. $PO_2$ remained at 93-94%, RF=20, CFq=70, and BP=133/75. No clinical changes were observed after 2 h.

Then, the subject received a nebulization treatment with 3 ml of 100 mM arginine solution at pH 8.5. The $PO_2$ increased from 94 to 98% for 30 seconds and fell rapidly (decreased to 93% at the end of nebulization). RF=21, CFq=66.

Later, the subject received nebulization treatment with 3 ml of Ibu-Arg solution at pH 8. Immediately after nebulization: $PO_{2=97}$%, RF=19, CFq=65, and BP=134/75. Six hours after nebulization: $PO_{2=96}$%, RF=20, CFq=69, and BP=132/73.

Note: In this case, the amount of $Na_2CO_3$ added to the Ibu-Arg solution described in Example 2 was reduced so the final pH of the solution was 8.

Finally, the subject received nebulization treatment with 3 ml of Ibu-Arg solution at pH 8.5. Immediately after nebulization: $PO_2$=96%, and CFq=64. Six hours after nebulization: $PO_2$=96%, RF=24, CFq=78, and BP=135/75. Eight hours after nebulization $PO_2$ was 95-98%, RF=17, CFq=75, and BP=130/70.

Example 13: Effect of Nebulization with Arginine Solution at pH 7.0 and 8.5 and with the Formulation of the Present Invention at pHs 8.5 and 9 on the $O_2$ Saturation, Heart Rate, Respiratory Rate, and Blood Pressure in a Subject with COPD Subject 13.

Gender: male.

Admission date: 28 Sep. 2021.

Age: 72 years old; weight: 120 kg; height: 1.78.

COVID-19 test: negative (−).

Diagnosis: COPD 15 years ago, dyspnea on exertion grade 2/3.

Pathological personal history: hernia surgery; diabetes (−); HBP (−); COVID-19 (−); obesity (+).

Toxic background: tobacco (+) (20 cigarettes a day for 50 years); alcohol (−); drugs (−).

Treatment: neumoterol (micronized budesonide/micronized formoterol fumarate dihydrate) at night.

Clinical Evolution of Subject 13:

Basal state: $PO_2$=88-93%, RF=25, CFq=84, and BP=157/95. Observations: bibasilar crackles.

The subject received a nebulization treatment with 3 ml of 100 mM arginine solution at pH 7. $PO_2$ remained at 92-93%. No changes were observed.

Then, the subject received a nebulization treatment with 3 ml of 100 mM arginine solution at pH 8.5. After 5 min, the $PO_2$ increased from 94% to 98% and decreased to 93% at the end of nebulization.

Later, the subject received nebulization treatment with 3 ml of Ibu-Arg solution at pH 8.5. Immediately after nebulization: $PO_2$ increased from 93% to 98-100%, RF=24, CFq=85, and BP=130/87. Six hours after nebulization: $PO_2$=97%, RF=21, CFq=89, and BP=134/88. Eight hours after nebulization: $PO_2$=94%, RF=22, CFq=82, and BP=134/90.

Finally, the subject received nebulization treatment with 3 ml of Ibu-Arg solution at pH 9. Immediately after nebulization: $PO_2$=99%, RF=23, CFq=83, and BP=132/89. Six hours after nebulization: $PO_2$=96%, RF=22, CFq=80, and BP=133/89.

Note: In this case, the amount of $Na_2CO_3$ added to the favorite Ibu-Arg solution described in Example 2 was increased so the final pH of the solution was 9.

Example 14: Effect of Nebulization with Hypertonic Alkaline Ibuprofen (AHI) Solution and the Formulation of the Present Invention (Ibu-Arg Solutions) Versus on $O_2$ Saturation in Subjects Suffering from Bilateral Pneumonia by SARS-CoV-2

Three subjects suffering from bilateral pneumonia by SARS-CoV-2, PCR (+), were treated. First, they were nebulized with AHI solution every 8 h for 48 hours, then the response was measured through changes in pulse oximetry. Subsequently, they were nebulized with Ibu-Arg solutions with different arginine concentrations. These solutions were prepared by varying the amount of arginine hydrochloride added to the formulation described in Example 2. Again at the end of nebulization, the response was measured through changes in pulse oximetry.

TABLE 3

Clinical evolution of subjects 14, 15, and 16.

| Subject | Treatment 1 | $PO_2$ pre and post-treatment 1 | Treatment 2 | $PO_2$ pre and post-treatment 2 |
|---|---|---|---|---|
| 14 | 5 mL of AHI solution every 8 h for 48 h. | 88-90 | Ibu-Arg solution (arginine 25 mM). Only one nebulization. | 90-93 |
| 15 | 5 mL of AHI solution every 8 h for 48 h. | 90-91 | Ibu-Arg solution (arginine 50 mM). Only one nebulization. | 90-95 |
| 16 | 5mL of AHI solution every 8 h for 48 h. | 88-91 | Ibu-Arg solution (arginine 100 mM). Only one nebulization. | 92-99 |

Example 15: In Vivo Determination of Superoxide Anion Generation in Murine Macrophages The mechanism of oxidative stress, which has been widely recognized as a key factor in the genesis and development of various lung diseases, is inhibited by the formulation of the present invention. To measure the synergistic effect of the ibuprofen-arginine combination on oxidative stress and determine its synergy ranges, the inhibitory effect of reactive oxygen species in living cells stimulated by LPS that have been exposed to the formulation was studied, thus correlating the reduction of ROS with the therapeutic effect of the formulation of the present invention.

The selected method measures the fluorescence of DHE generated from its interaction with superoxide anion ($O_2^-$) to determine the inhibitory effect of the different formulations on the generation of $O_2^-$ in murine macrophages that have been stimulated with LPS. This method has been selected because, as Chen et al. [Chen, J., et al. (2013). Analysis of kinetics of dihydroethidium fluorescence with superoxide using xanthine oxidase and hypoxanthine assay. Annals of Biomedical Engineering, 41 (2), 327-337. https://doi.org/10.1007/s10439-012-0653-x], can be used to detect $O^{2-}$ concentration without interference from pathways in the cellular system and is useful for determining cumulative $O_2^-$ concentrations and for predict damage to cellular systems.

Method and Materials

The commercial cell line RAW 264.7 (murine macrophages) of passage number between 20-30 was used. Sixty thousand cells per well of a 96-well plate were seeded and incubated overnight with DMEM/F12 growth medium (Gibco) supplemented with 0.1% fetal bovine serum (Internegocios) and antibiotic/antimycotic mixture. The next morning, the growth medium was removed, the cells were washed with phosphate buffer (PBS) and incubated for 30 min at 37° C. with dihydroethidium fluorescent dye (DHE; Invitrogen) at a final concentration of 5 M in PBS. After this incubation, the cells were washed and incubated for one hour with the solutions to be tested: Ibuprofen (10, 50, 100 μM), Arginine (5-100 μM; SIGMA) and their combinations, all prepared in PBS solution. Ibuprofen in PBS solutions were obtained by dilution of the formulation described in Example 1 and arginine in PBS solutions were prepared with arginine hydrochloride. Apocynin (50 μM; SIGMA), an uncoupling agent of NAD(P)H oxidase, an inhibitor of superoxide anion production, was included as a control.

After this incubation, basal fluorescence was measured on a Fluoroskan Ascent plate reader, Labsystems using $\lambda$ex=485 nm and $\lambda$em=538 nm. LPS (25 μg/mL: SIGMA) was immediately added to each well, leaving unstimulated controls, and incubated at 37° C. for 60 minutes. The fluorescence of the plate was then re-recorded using the same filter as in the basal condition.

For the analysis of the results, the value corresponding to the basal fluorescence for each well was subtracted from each final time value.

Statistical analysis was performed using GraphPad Prism 6.0 software. A p-value $<0.05$ was considered statistically significant. One-way ANOVA followed by Tukey's multiple comparisons post-test was performed. Data represent the mean±standard error of the mean (SEM) of two independent experiments.

Example 16: Inhibiting Effect of Alkaline Hypertonic Ibuprofen Solution and Arginine Solution on the Generation of Superoxide Anion in Macrophages Stimulated with Lipopolysaccharide (LPS)

Murine macrophages were stimulated with LPS (25 μM/mL) and treated with arginine 50 μM alone or with different concentrations of alkaline hypertonic ibuprofen (10, 50, and 100 μM) in PBS saline solution. The cells were loaded with dihydroethidium (DHE) for 30 min at 37° C. and after 60 min of stimulation, normalized fluorescence was determined with the basal reading.

Figure 3:
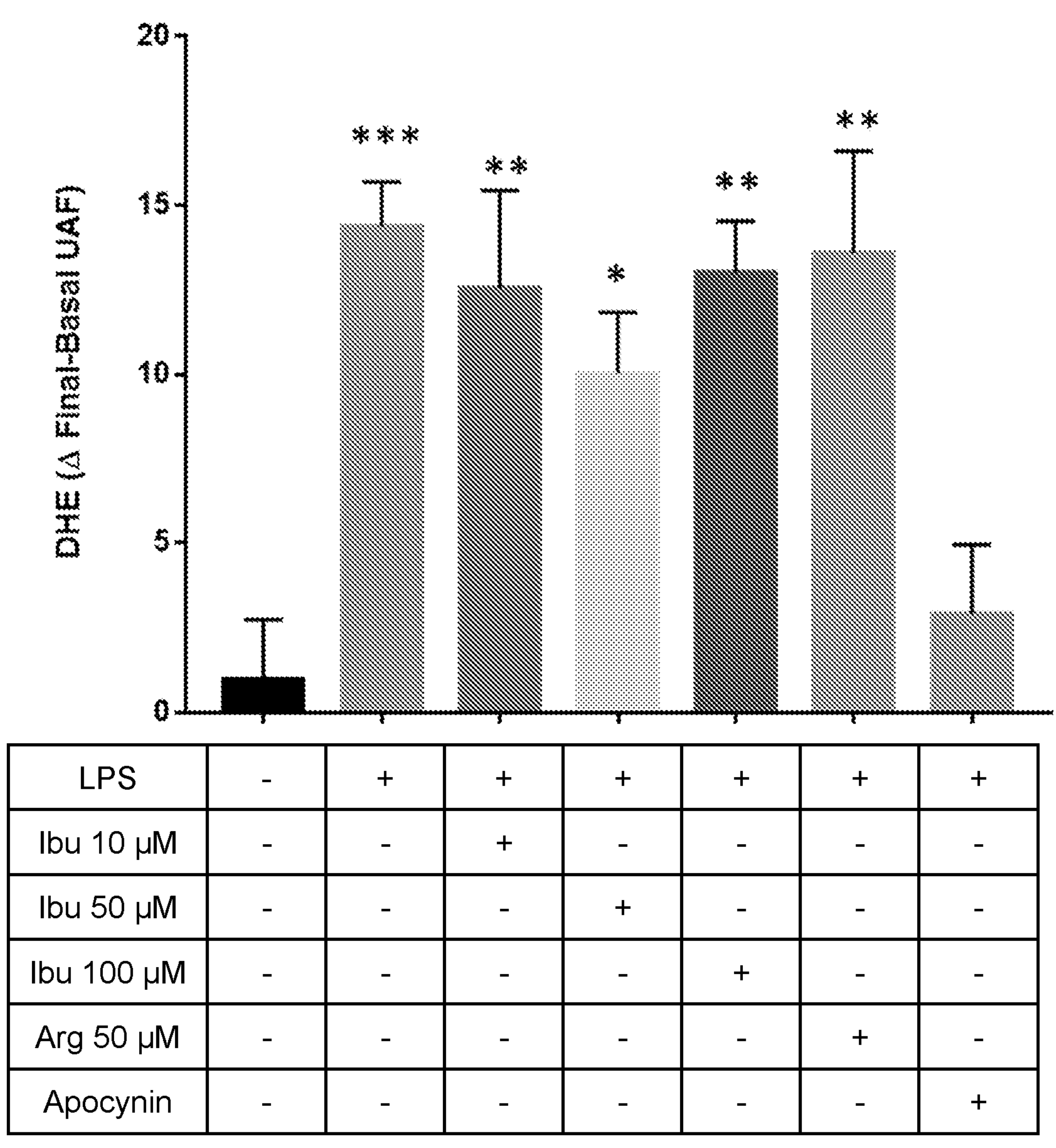
FIG. 3. Inhibiting effect of alkaline hypertonic ibuprofen solutions and arginine solution on the generation of superoxide anion in macrophages stimulated with LPS. $*p<0.05$, $p<0.01$, $*p<0.001$ vs. control.

As it can be observed from FIG. 3, LPS (25 μM/mL) stimulates the generation of superoxide anion in murine macrophages. However, this effect is not inhibited by Ibuprofen (Ibu 10, Ibu 50, Ibu 100 μM) alone or Arginine (Arg 50 μM) alone. Apocynin (50 μM) was used as a specific inhibitor of NADPH oxidase, an enzyme that generates $O_2^-$.

Example 17: Inhibiting Effect of Alkaline Hypertonic Ibuprofen Solution with Arginine on the Generation of Superoxide Anion in Macrophages Stimulated with LPS Murine macrophages were stimulated with LPS (25 μM/mL) and treated with alkaline hypertonic Ibuprofen 10 μM alone or combined with different concentrations of arginine (5, 10, 20, 50, 65, 85 and 100 μM) in PBS saline solution. The cells were loaded with dihydroethidium (DHE) for 30 min at 37° C. and after 60 min of stimulation, normalized fluorescence was determined with the basal reading.

Figure 4:
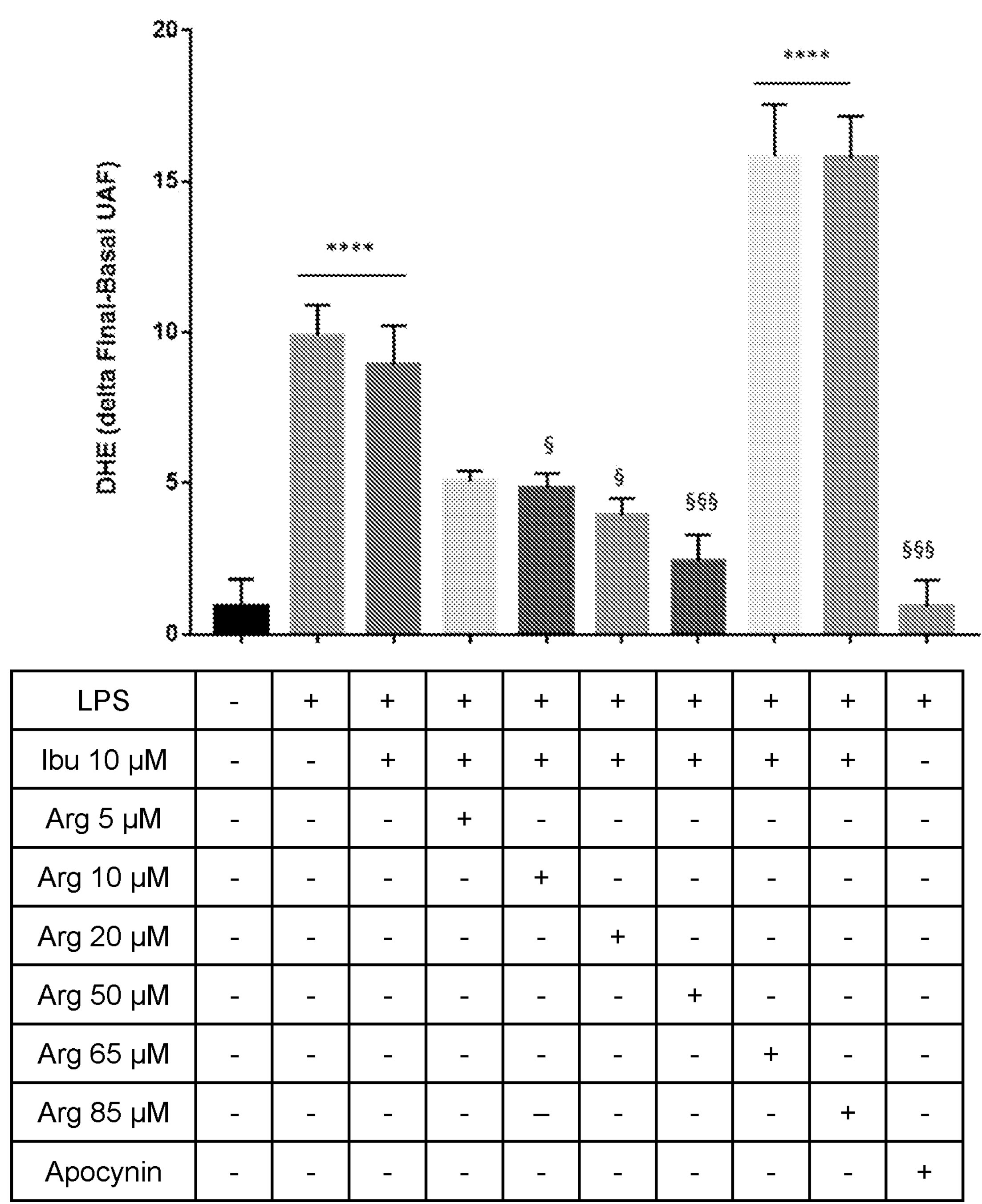
FIG. 4. Inhibiting effect of alkaline hypertonic ibuprofen (10 μM) solution alone or with different amounts of arginine (5, 10, 20, 50, 65, 85, and 100 μM) on the generation of superoxide anion in macrophages stimulated with LPS. ($****p<0.0001$ vs. control; § $p<0.05$, § § § $p<0.001$ vs. LPS).

As It can be concluded from FIG. 4, arginine/ibuprofen molar ratios greater than 1 and lower than 6.5 generate a marked synergic effect, inhibiting the LPS-stimulated increase in the concentration of superoxide anion.

Examples 16 and 17 clearly demonstrate that the formulation of the present invention presents a new synergistic effect reducing the concentration of ROS in living cells. However, it only happens when arginine is in a solution together with the ibuprofen molecule and in a certain concentration range.

The invention claimed is:

1. A pharmaceutical composition to be applied on the pulmonary epithelium for the treatment of respiratory diseases, comprising ibuprofen, arginine, solubilized in a hypertonic aqueous solution at a pH between 7.5 and 9.5 wherein the arginine/ibuprofen molar ratio is lower than 6.5.

2. The pharmaceutical composition of claim 1, wherein the arginine/ibuprofen molar ratio is greater than 1.

3. The pharmaceutical composition of claim 1, wherein the ibuprofen is in a concentration from 10 mM to 50 mM.

4. The pharmaceutical composition of claim 1, wherein the ibuprofen is racemic.

5. The pharmaceutical composition of claim 1, wherein the ibuprofen is the S enantiomer.

6. The pharmaceutical composition of claim 1, wherein the ibuprofen is the R enantiomer.

7. The pharmaceutical composition of claim 1, wherein said ibuprofen comprises as a counterion the monovalent cation selected from the group consisting of sodium, potassium, lithium, arginate, lysinate, histidinate and combinations thereof.

8. The pharmaceutical composition of claim 1, wherein said arginine comprises a concentration from 10 mM to 250 mM.

9. The pharmaceutical composition of claim 1, further comprising a pH in aqueous solution from 8.0 to 9.0.

10. The pharmaceutical composition of claim 9, wherein the pH in aqueous solution is 8.5.

11. The pharmaceutical composition of claim 1, wherein the composition is in nebulizer or inhalation form.

12. The pharmaceutical composition of claim 1, wherein the composition is in liquid, powder or lyophilized state.

13. The pharmaceutical composition of claim 1, wherein said composition is hypertonic comprising a salt in a concentration from 0.3 to 2.0 M.

14. The pharmaceutical composition of claim 1, wherein said composition is hypertonic comprising a salt in a concentration from 0.4 to 1.1 M.

15. The pharmaceutical composition of claim 1, wherein said composition is hypertonic comprising a salt in a concentration from 0.5 to 1.0 M.

16. The pharmaceutical composition of claim 13, wherein said salt is selected from the group consisting of sodium chloride, potassium chloride, sodium carbonate and combinations thereof.

17. The pharmaceutical composition of claim 16, wherein said salt is NaCl.

18. A manufacturing process of a pharmaceutical composition of claim 1, wherein said process comprises the following steps:

a) mixing said ibuprofen in its acid state with aqueous solution of $Na_2CO_3$ at more than 40° C. and stirring to maintain its suspension;

b) adding said arginine on the step a);

c) adding NaOH or $Na_2CO_3$ to reach a pH value from 7.5 to 9.5 and stirring to allow a complete solubilization of said ibuprofen and arginine to obtain a concentration between 1 and 100 mg/mL for ibuprofen and between 5 and 100 mg/mL for basic amino acid;

d) adding said salt suitable for human consumption to the preparation of said step c), in a concentration from 0.3 to 1.0 M and;

e) filtering the preparation in said step d), through a 0.22 micron pore filter.

19. The process of claim 18, further comprising the following step:

f) lyophilizing the filtered solution in said step e).

20. The process of claim 19, further comprising the following step:

g) at the time to be applied to a patient in need thereof, resuspending the lyophilized composition of said step f) in water or in a 2.5% of glucose solution.

21. A method for treating lung disease comprising administering an effective amount of the pharmaceutical composition of claim 1 to the pulmonary epithelium of the subject in need thereof.

22. The method of claim 21, wherein said pharmaceutical composition is administered to the subject as a nebulized solution.

23. The method of claim 22, wherein between 1 mL and 25 mL of said pharmaceutical composition is administered to the subject.

24. The method of claim 22, wherein between 1 mL and 10 mL of said pharmaceutical composition is administered to the subject.

25. The method of claim 22, wherein between 1 mL and 5 mL of said pharmaceutical composition is administered to the subject.

26. The method of claim 22, wherein 3 mL of said pharmaceutical composition is administered to the subject.

27. The method of claim 21, wherein said lung disease is selected from the group consisting of asthma, chronic obstructive pulmonary disease (COPD), cystic fibrosis (CF), pulmonary hypertension, bronchopulmonary dysplasia, acute respiratory distress syndrome (ARDS), respiratory syndrome coronavirus 2 (SARS-CoV-2), respiratory viral, mycotic or bacterial infection, bilateral pneumonia, and bronchiectasis.

28. The method of claim 21, wherein the subject is hypoxic.

29. The method of claim 28, wherein the subject has a pulse-oximetry blood-oxygen saturation level of less than 92%.

30. The method of claim 21, wherein the subject has a respiratory rate of 21-25 breaths/minute.

31. The method of claim 21, wherein the subject has a respiratory rate of 25-30 breaths/minute.

32. The method of claim 21, wherein the subject has a respiratory rate of 30-40 breaths/minute.

33. The method of claim 21, wherein the subject has a respiratory rate over 41 breaths/minute.

34. The method of claim 21, wherein the subject has a pulse rate of 91-110 beats/minute.

35. The method of claim 21, wherein the subject has a pulse rate of 111-130 beats/minute.

36. The method of claim 21, wherein the subject has a pulse rate of over 131 beats/minute.

37. The method of claim 21, wherein the subject has a NEWS2 Score of 0-4.

38. The method of claim 21, wherein the subject has a NEWS2 Score of 5-6.

39. The method of claim 21, wherein the subject has a NEWS2 Score of 7 or greater.

40. The method of claim 21, wherein the subject is intubated.

41. The method of claim 21, wherein the subject is pre-intubation.

42. The method of claim 21, wherein the subject is non-hypoxic.

* * * * *